(12) United States Patent
Kubota et al.

(10) Patent No.: US 8,318,995 B2
(45) Date of Patent: *Nov. 27, 2012

(54) ASYMMETRIC PYRENE DERIVATIVE AND ORGANIC ELECTROLUMINESCENCE DEVICE EMPLOYING THE SAME

(75) Inventors: Mineyuki Kubota, Sodegaura (JP); Masakazu Funahashi, Sodegaura (JP); Chishio Hosokawa, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/795,216

(22) Filed: Jun. 7, 2010

(65) Prior Publication Data

US 2010/0308718 A1  Dec. 9, 2010

Related U.S. Application Data

(63) Continuation of application No. 11/282,582, filed on Nov. 21, 2005, now Pat. No. 7,763,761, which is a continuation of application No. PCT/JP2005/008494, filed on May 10, 2005.

(30) Foreign Application Priority Data

May 27, 2004 (JP) .................................. 2004-157571

(51) Int. Cl.
  *C07C 13/615* (2006.01)
  *C07C 15/20* (2006.01)
  *H01J 1/62* (2006.01)

(52) U.S. Cl. .............................. 585/22; 585/26; 313/504

(58) Field of Classification Search .................. None
  See application file for complete search history.

(56) References Cited

U.S. PATENT DOCUMENTS

| | | | |
|---|---|---|---|
| 6,203,933 B1 | 3/2001 | Nakaya et al. | 428/690 |
| 6,534,199 B1* | 3/2003 | Hosokawa et al. | 428/690 |
| 6,635,364 B1 | 10/2003 | Igarashi | 428/690 |
| 7,763,761 B2* | 7/2010 | Kubota et al. | 585/26 |
| 2002/0063988 A1 | 5/2002 | Shibayama | 360/375 |
| 2002/0177009 A1* | 11/2002 | Suzuki et al. | 428/690 |
| 2004/0076852 A1 | 4/2004 | Cheng et al. | 428/690 |
| 2004/0137270 A1* | 7/2004 | Seo et al. | 428/690 |
| 2005/0233165 A1 | 10/2005 | Ido et al. | 428/690 |
| 2005/0238910 A1 | 10/2005 | Ionkin et al. | 428/690 |
| 2006/0154105 A1 | 7/2006 | Yamamoto et al. | 428/690 |

FOREIGN PATENT DOCUMENTS

| | | |
|---|---|---|
| EP | 1 718 124 | 11/2006 |
| EP | 0 864 567 A1 | 9/2009 |
| JP | 3-200889 | 9/1991 |
| JP | 7-138561 | 5/1995 |
| JP | 08-199162 | 8/1996 |
| JP | 8-239655 | 9/1996 |
| JP | 2000-273055 | 10/2000 |
| JP | 2001-118682 | 4/2001 |
| JP | 2002-63988 A | 2/2002 |
| JP | 2002-250684 | 2/2002 |
| JP | 2004-002297 | 1/2004 |
| JP | 2004-67528 | 3/2004 |
| JP | 2004-75567 | 3/2004 |
| JP | 2004-83481 | 3/2004 |
| WO | WO 2004/018587 A1 | 3/2004 |

OTHER PUBLICATIONS

Patent Abstracts of Japan, JP 2004-043349, Feb. 12, 2004.
J. Daub, et al., "Competiton Between Conformational Relaxation and Intramolecular Electron Transfer within Phenothiazine-Pyrene Dyads", Journal of Phisycical Chemistry, vol. 105, No. 23, 2001, pp. 5655-5665.
Peter Wahl, et al., "1,8,-Dipyrenylnaphthalenes: Syntheses, Molecular Structure, and Spectroscopic Properties", Chem. Ber., vol. 117, No. 1, 1984, pp. 260-276.
C.W. Tang, et al., "Organic electroluminescent diodes", App. Phys. Lett., vol. 51, No. 12, Sep. 21, 1987, pp. 913-915.
Office Action issued Jan. 20, 2011, in Korean Patent Application No. 10-2006-7024933.

* cited by examiner

*Primary Examiner* — Camie Thompson
(74) *Attorney, Agent, or Firm* — Oblon, Spivak, McClelland, Maier & Neustadt, L.L.P.

(57) ABSTRACT

Asymmetric pyrene derivatives having specific structure. An organic EL device comprising at least one organic thin film layer including a light emitting layer sandwiched between a pair of electrode consisting of an anode and a cathode, wherein the organic thin film layer comprises at least one kind selected from the aforementioned asymmetric pyrene derivatives singly or as a component of mixture thereof. An organic EL device exhibiting a great efficiency of light emission and having a long lifetime, and also asymmetric pyrene derivatives for realizing the organic EL device are provided.

21 Claims, No Drawings

ASYMMETRIC PYRENE DERIVATIVE AND ORGANIC ELECTROLUMINESCENCE DEVICE EMPLOYING THE SAME

CROSS-REFERENCE TO RELATED APPLICATIONS

The present application is a continuation application of U.S. Ser. No. 11/282,582, filed Nov. 21, 2005 now U.S. Pat. No. 7,763,761, which is a continuation of PCT/JP2005/008494, filed on May 10, 2005, which published as WO 2005/115950 on Dec. 8, 2005, and claims priority to Japan Application No. 2004-157571, filed May 27, 2004.

TECHNICAL FIELD

The present invention relates to an asymmetric pyrene derivative and an organic electroluminescence ("electroluminescence" will be occasionally referred to as "EL", hereinafter) device employing the same, more particularly, to an organic EL device exhibiting a great efficiency of light emission and having a long lifetime, and also to the asymmetric pyrene derivative for realizing the organic EL device.

BACKGROUND ART

An organic electroluminescence device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang et al. of Eastman Kodak Company (C. W. Tang and S. A. Vanslyke, Applied Physics Letters, Volume 51, Pages 913, 1987), many studies have been conducted on organic EL devices using organic materials as the constituting materials. Tang et al. used a laminate structure using tris(8-hydroxyquinolinol aluminum) for the light emitting layer and a triphenyldiamine derivative for the hole transporting layer. Advantages of the laminate structure are that the efficiency of hole injection into the light emitting layer can be increased, that the efficiency of forming excited particles which are formed by blocking and recombining electrons injected from the cathode can be increased, and that excited particles formed among the light emitting layer can be enclosed. As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

As the light emitting material of the organic EL device, chelate complexes such as tris(8-quinolinolato)aluminum, coumarine derivatives, tetraphenylbutadiene derivatives, bis-styrylarylene derivatives and oxadiazole derivatives are known. It is reported that light in the visible region ranging from blue light to red light can be obtained by using these light emitting materials, and development of a device exhibiting color images is expected (refer to, for example, Patent literature 1, Patent literature 2, and Patent literature 3).

Further, a device using asymmetrical pyrene derivative as the light emitting material is disclosed in Patent literatures 4 to 7, and a device using an asymmetrical anthracene derivative as the light emitting material is disclosed in Patent literature 8. Although these derivatives are used as the material for emitting blue light, further improvements of the lifetime thereof have been desired. In addition, development of a derivative being not easily affected by oxidization has been desired because of low oxidative stability of existing derivatives.

Patent literature 1: Japanese Patent Application Laid-Open No. Heisei 8 (1996)-239655
Patent literature 2: Japanese Patent Application Laid-Open No. Heisei 7 (1995)-138561
Patent literature 3: Japanese Patent Application Laid-Open No. Heisei 3 (1991)-200289
Patent literature 4: Japanese Patent Application Laid-Open No. 2001-118682
Patent literature 5: Japanese Patent Application Laid-Open No. 2002-63988
Patent literature 6: Japanese Patent Application Laid-Open No. 2004-75567
Patent literature 7: Japanese Patent Application Laid-Open No. 2004-83481
Patent literature 8: International PCT publication No. WO 04/018587

DISCLOSURE OF THE INVENTION

The present invention has been made to overcome the above problems and has an objective of providing an organic electroluminescence device exhibiting a great efficiency of light emission and having a long lifetime, and also to an asymmetric pyrene derivative for realizing the organic EL device.

As a result of intensive researches and studies to achieve the above objective by the present inventors, it was found that employing an asymmetric derivative represented by any of following general formulae from (1) to (3) as a constituting material for an organic thin film of an organic EL device enables to provide the organic EL device exhibiting a great efficiency of light emission and having a long lifetime.

Therefore, the present invention provides an asymmetric pyrene derivative represented by any of the following general formulae (1) to (3):

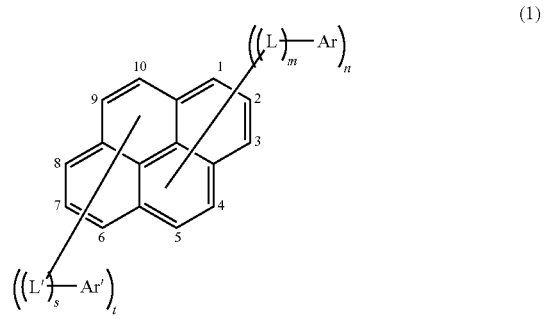

In the general formula (1), Ar and Ar' each represents a substituted or unsubstituted aromatic group having 6 to 50 ring carbon atoms;

L and L' each represents a substituted or unsubstituted phenylene group, a substituted or unsubstituted naphthalenylene group, a substituted or unsubstituted fluorenylene group or a substituted or unsubstituted dibenzosilolylene group;

m represents an integer of 0 to 2, n represents an integer of 1 to 4, s represents an integer of 0 to 2 and t represents an integer of 0 to 4; and, L or Ar bonds to any one of 1 to 5 position of pyrene, also L' or Ar' bonds to any one of 6 to 10 position thereof, however, when n+t is an even number, Ar, Ar', L and L' satisfy a following requirement (1) or a requirement (2):

(1) Ar≠Ar' and/or L≠L' (wherein ≠ means that each group has a different structure)

(2) when Ar=Ar' and L=L'
(2-1) m≠s and/or n≠t, or
(2-2) when m=s and n=t,
(2-2-1) both L and L' or pyrene bond respectively to a different position of Ar and Ar' or (2-2-2) both L and L' or pyrene bond respectively to the same position of Ar and Ar' excluding a case where both L and L' or both Ar and Ar' bond respectively to 1 and 6, or 2 and 7 positions thereof.

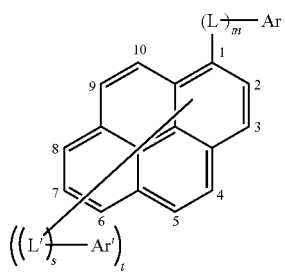

(2)

In the general formula (2), Ar, Ar', L, L', m, s and t are the same with the aforementioned.

L' or Ar' bonds to any one of 2 to 10 positions of the pyrene, however, when t is an odd number, Ar, Ar', L and L' satisfy a following requirement (1') or a requirement (2'):

(1') Ar≠Ar' and/or L≠L' (wherein ≠ means that each group has a different structure)

(2') when Ar=Ar' and L=L'
(2-1') m≠s and/or t≠1, or
(2-2') when m=s and t=1,
(2-2-1') both L and L' or pyrene each bonds respectively to different positions of Ar and Ar', or
(2-2-2') both L and L' or pyrene each bonds to the same positions of Ar and Ar' excluding a case where L' or Ar' bonds to 6 position thereof.

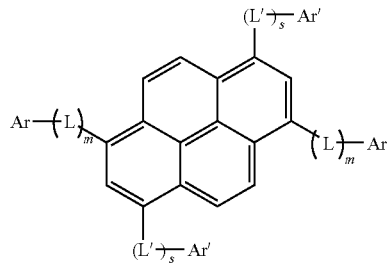

(3)

In the general formula (3), Ar, Ar', L, L', m and s are the same with aforementioned.

Moreover, the present invention provides an organic EL device comprising at least one organic thin film layer including a light emitting layer sandwiched between a pair of electrode consisting of an anode and a cathode, wherein the organic thin film layer comprises at least one kind selected from the aforementioned asymmetric pyrene derivatives singly or as a component of mixture thereof.

An organic EL device containing an asymmetric pyrene derivative of the present invention exhibits a great efficiency of light emission and has a long lifetime.

THE PREFERRED EMBODIMENT TO CARRY OUT THE INVENTION

The present invention provides an asymmetric pyrene derivative represented by a following general formula (1):

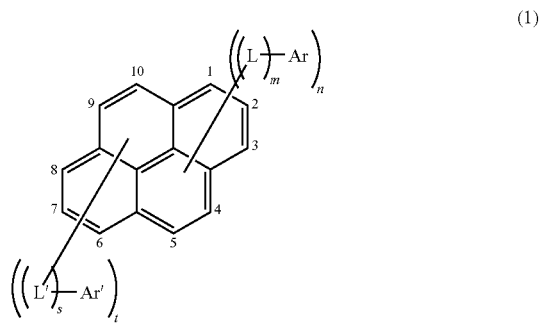

(1)

In the general formula (1), Ar and Ar' each represents a substituted or unsubstituted aromatic group having 6 to 50 ring carbon atoms.

Examples of the substituted or unsubstituted aromatic group include phenyl group, 1-naphthyl group, 2-naphthyl group, 1-anthryl group, 2-anthryl group, 9-anthryl group, 9-(10-phenyl) anthryl group, 9-(10-naphtyl-1-yl) anthryl group, 9-(10-naphtyl-2-yl) anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, 3-methyl-2-naphthyl group, 4-methyl-1-naphthyl group, 4-methyl-1-anthryl group and the like.

Among the aforementioned, preferred examples includes phenyl group, 1-naphthyl group, 2-naphthyl group, 9-(10-phenyl) anthryl group, 9-(10-naphtyl-1-yl) anthryl group, 9-(10-naphtyl-2-yl) anthryl group, 9-phenanthryl group, 1-pyrenyl group, 2-pyrenyl group, 4-pyrenyl group, 2-biphenylyl group, 3-biphenylyl group, 4-biphenylyl group, o-tolyl group, m-tolyl group, p-tolyl group, p-t-butylphenyl group and the like.

Further, the aforementioned aromatic groups may be substituted by a substituent such as alkyl group (methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxy-isopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triamino-propyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyano-propyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopropyl group, cyclobutyl group, cyclopentyl group, cyclohexyl group, 4-methylcyclohexyl group, 1-adamanthyl group, 2-adamanthyl group, 1-norbornyl group, 2-norbornyl group), alkoxy group having 1 to 6 carbon atoms (ethoxy group, methoxy group, i-propoxy group, n-propoxy group, s-butoxy group, t-butoxy group, pentoxy group, hexyloxy group, cyclopentoxy group, cyclohexyloxy group and etc.), aryl group having 5 to 40 ring carbon atoms, amino group substituted by aryl group having 5 to 40 ring carbon atoms, ester group containing aryl group having 5 to 40 ring carbon atoms, ester group containing alkyl group having 1 to 6 carbon atoms, cyano group, nitro group, halogen atom and the like.

In the general formula (1), L and L' each represents a substituted or unsubstituted phenylene group, a substituted or unsubstituted naphtharenylene, a substituted or unsubstituted fluorenylene group or a substituted or unsubstituted a dibenzosilolylene group, and a substituted or unsubstituted phenylene group or a substituted or unsubstituted fluorenylene group is preferred.

In addition, the substituent thereof includes the same with the aforementioned aromatic groups.

In the general formula (1), m represents an integer of 0 to 2 (preferably 0 to 1), n represents an integer of 1 to 4 (preferably 1 to 2), s represents an integer of 0 to 2 (preferably 0 to 1) and t represents an integer of 0 to 4 (preferably 0 to 2), and, in the general formula (1), L or Ar bonds to any one of 1 to 5 positions of the pyrene, and also L' or Ar' bonds to any one of 6 to 10 positions thereof, however, when n+t is an even number, Ar, Ar', L and L' satisfy a following requirement (1) or a requirement (2):

(1) A r≠Ar' and/or L=L', wherein means ≠ that each group has a different structure, (2) when Ar=Ar' and L=L', (2-1) m≠s and/or n≠t, or (2-2) when m=s and n=t, (2-2-1) both L and L' or pyrene bond respectively to a different position of Ar and Ar' or (2-2-2) both L and L' or pyrene bond respectively to the same position of Ar and Ar' excluding a case where both L and L' or both Ar and Ar' bond respectively to 1 and 6, or 2 and 7 positions thereof.

Further, the asymmetric pyrene derivatives of the present invention include the compounds represented by a following general formula (2):

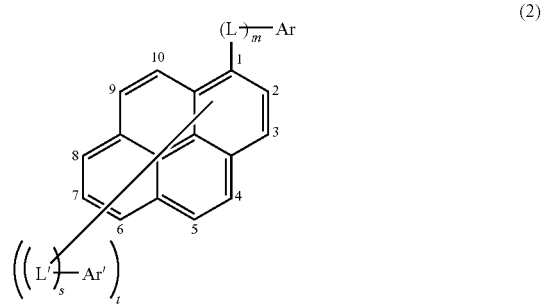

In the general formula (2), Ar, Ar', L, L', m, s and t are the same with the aforementioned. Further, preferable examples thereof and examples of the substituent thereof are the same with aforementioned. In addition, L' or Ar' bonds to any one of 2 to 10 positions of pyrene, however, in the general formula (2), when t is an odd number, Ar, Ar', L and L' satisfy a following requirement (1') or a requirement (2');

(1) Ar≠Ar' and/or L=L', wherein ≠ means that each group has a different structure, (2) when Ar=Ar' and L=L', (2-1') m≠s and/or t≠1, or (2-2') when m=s and t=1, (2-2-1') both L and L' or pyrene each bonds respectively to different positions of Ar and Ar', or (2-2-2') both L and L' or pyrene each bonds to the same positions of Ar and Ar' excluding a case where L' or Ar' bonds to 6 position thereof.

In addition, the asymmetric pyrene derivative of the present invention is preferably the compounds represented by a following general formula (3).

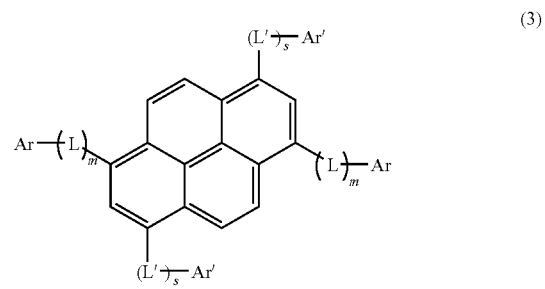

In the general formula (3), Ar, Ar', L, L', m and s are the same with the aforementioned, and preferable examples thereof and examples of the substituent thereof are the same with aforementioned.

Specific examples of the asymmetric pyrene derivatives represented by the general formulae (1) to (3) of the present invention include the following compounds, though not limited thereto.

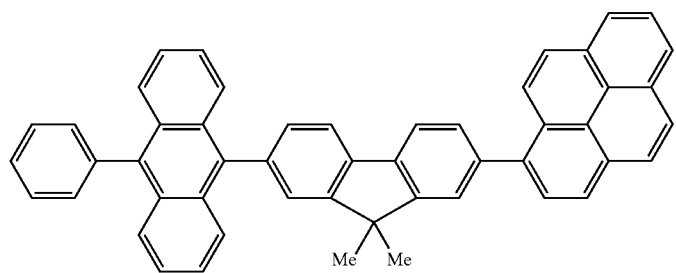
AN-1
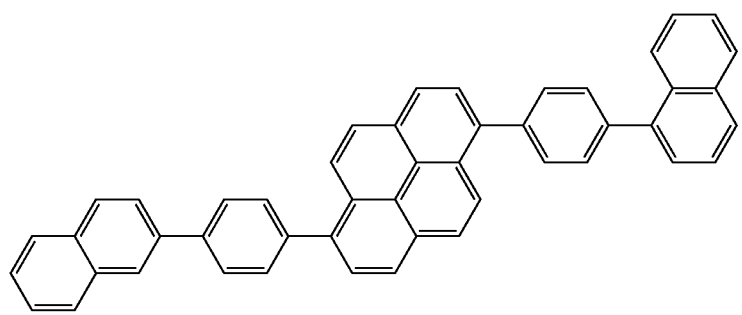
AN-2
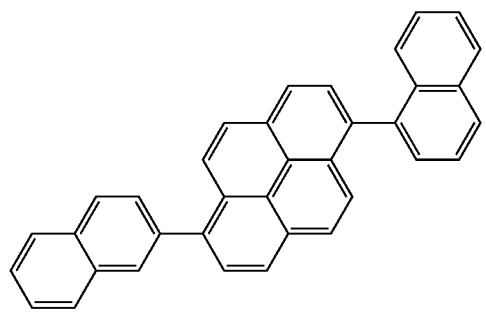
AN-3
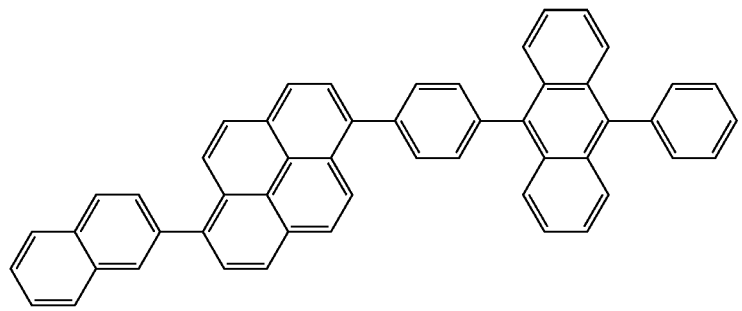
AN-4
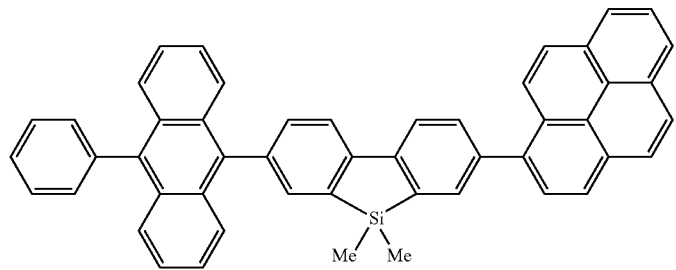
AN-5

-continued
AN-6
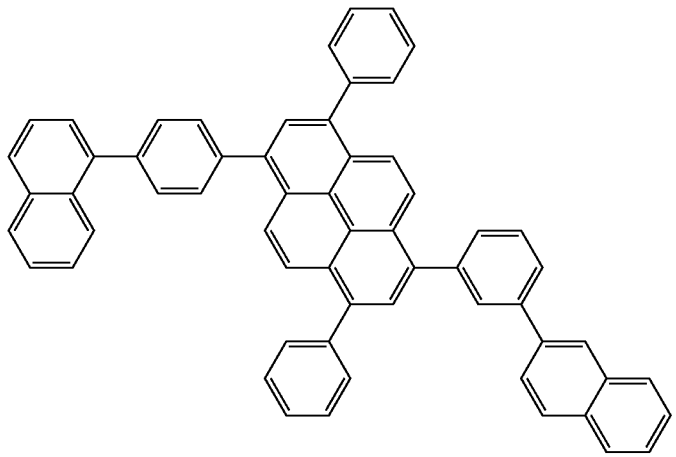
AN-7
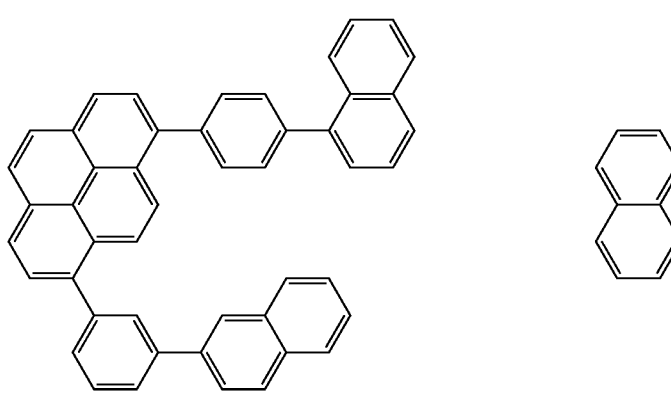
AN-8
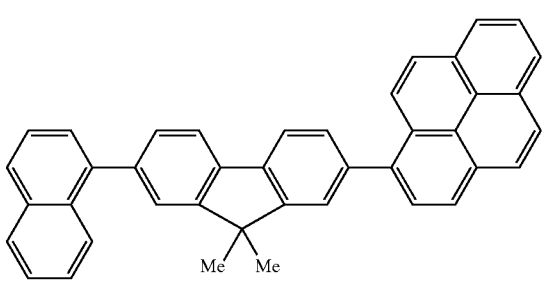
AN-9
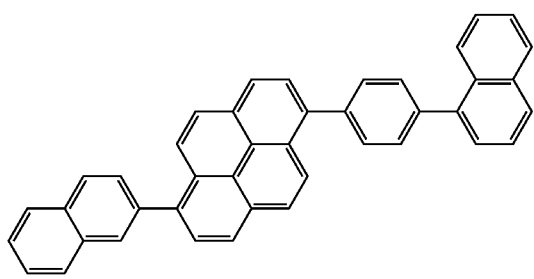
AN-10
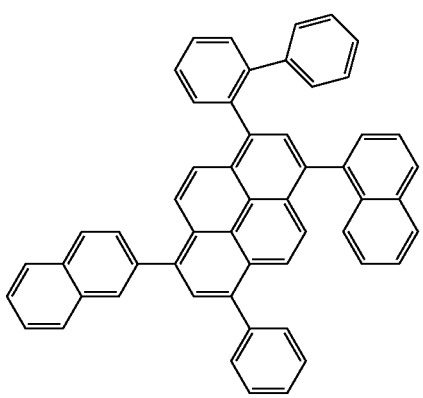
AN-11
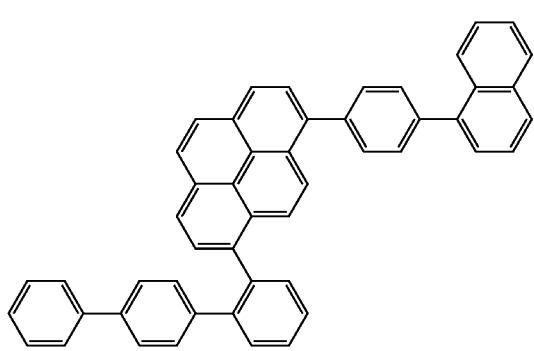
AN-12

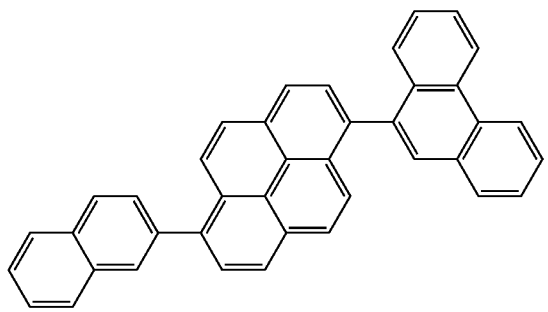
AN-13
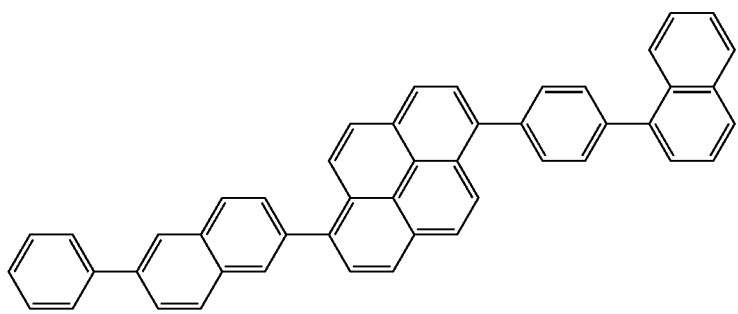
AN-14
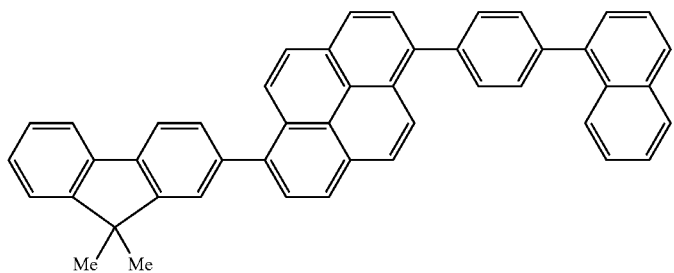
AN-15
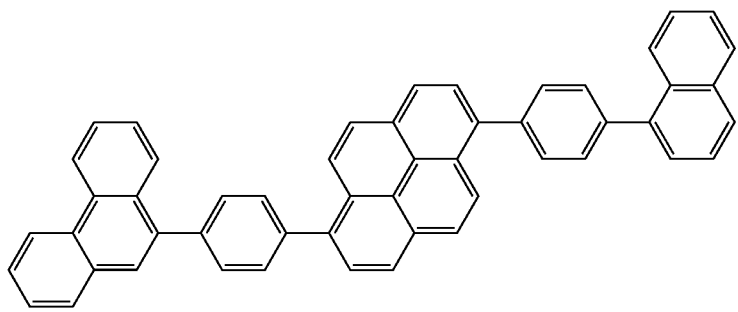
AN-16
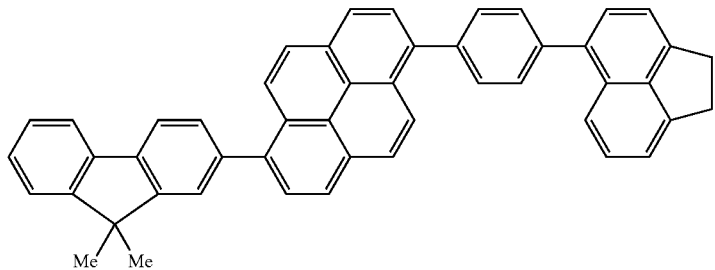
AN-17

AN-18
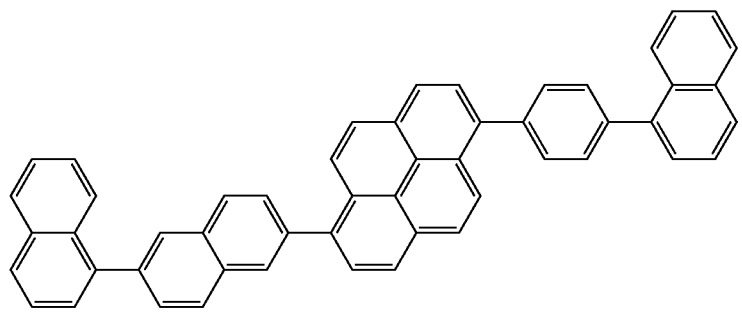
AN-19
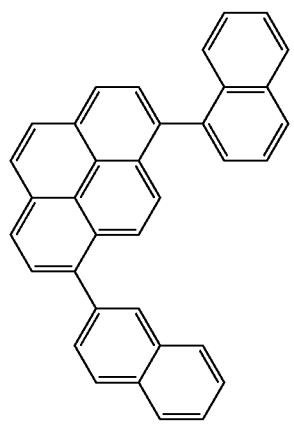
AN-20
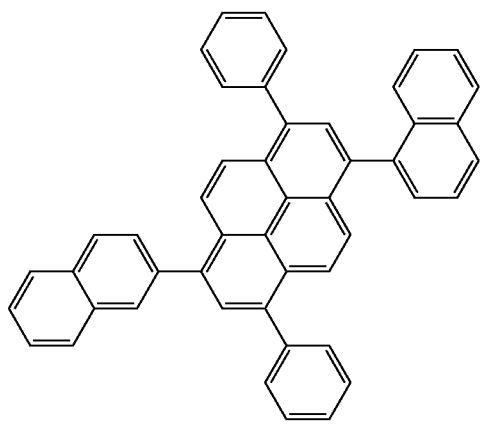
AN-21
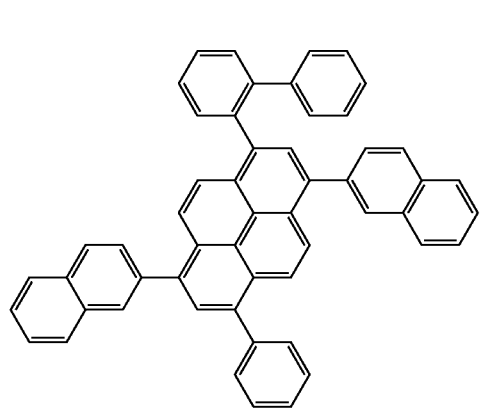
AN-22
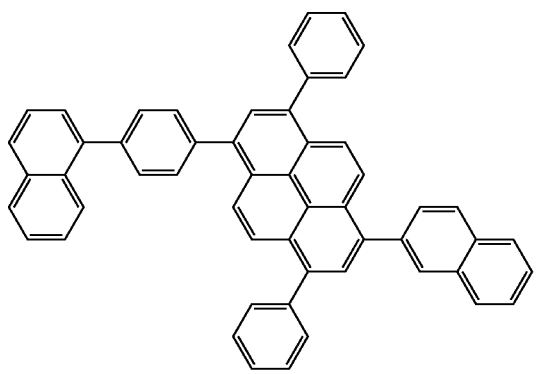
AN-23
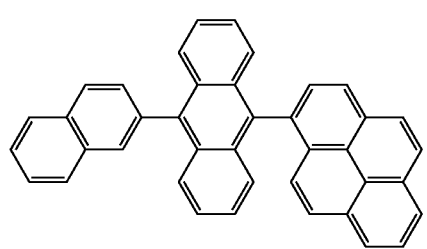
AN-24
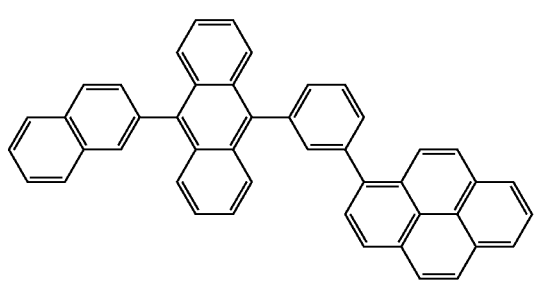

AN-25
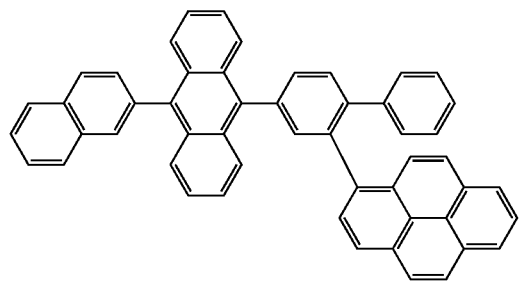
AN-26
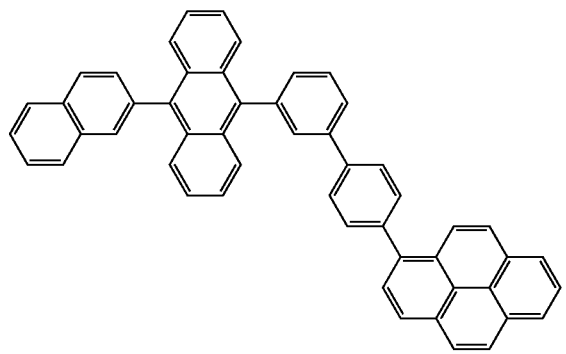
AN-27
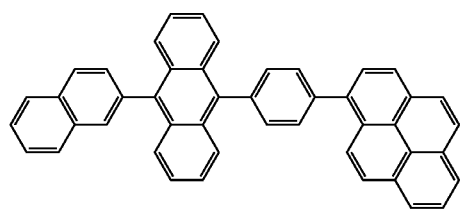
AN-28
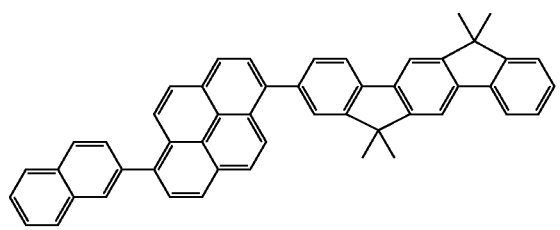
AN-29
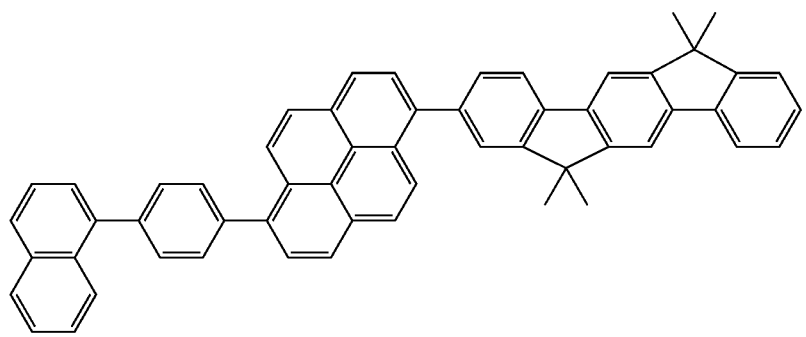
AN-30
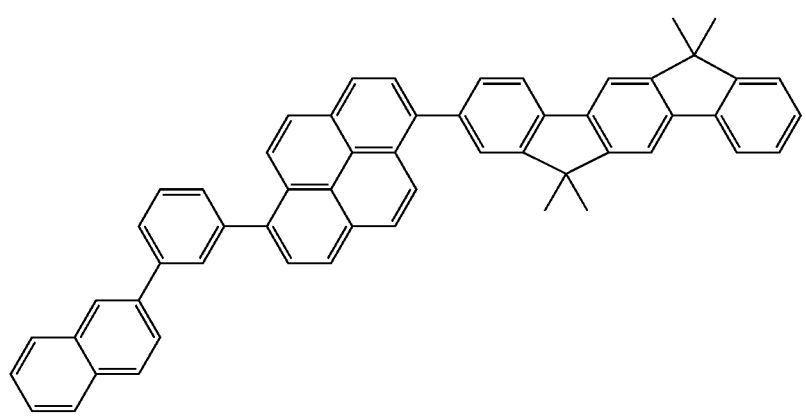

-continued
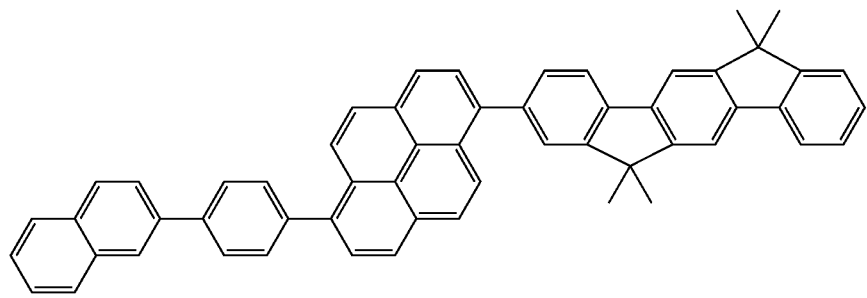
AN-31
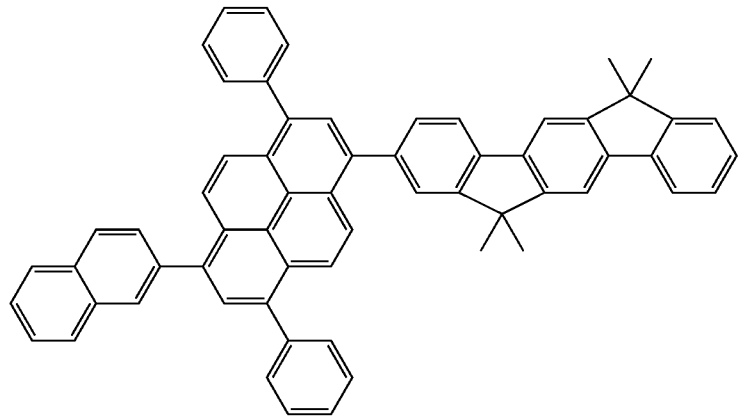
AN-32
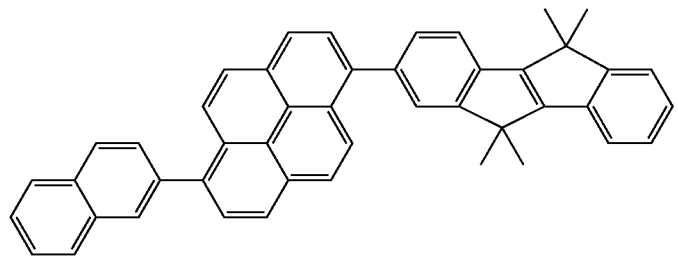
AN-33
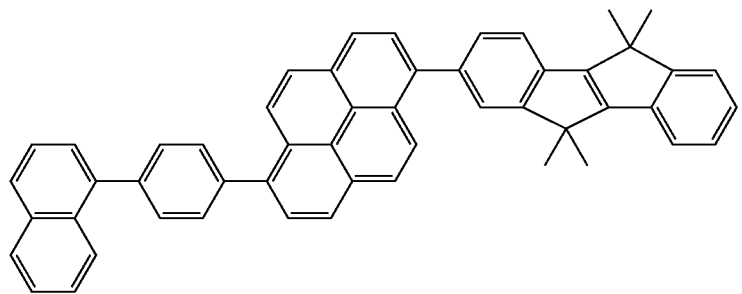
AN-34
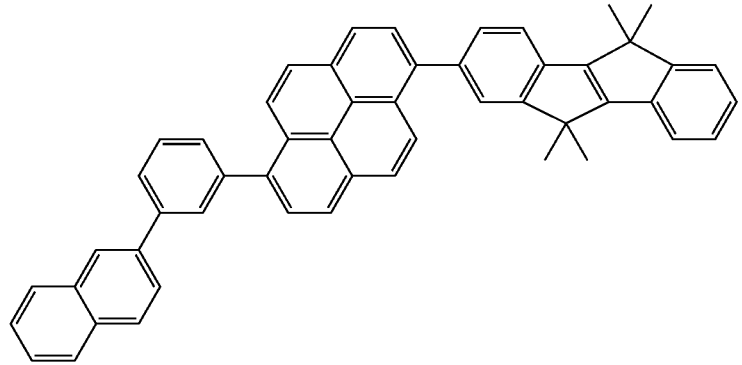
AN-35

AN-36

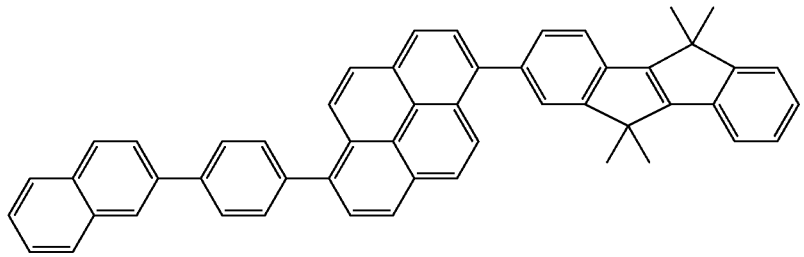

AN-37

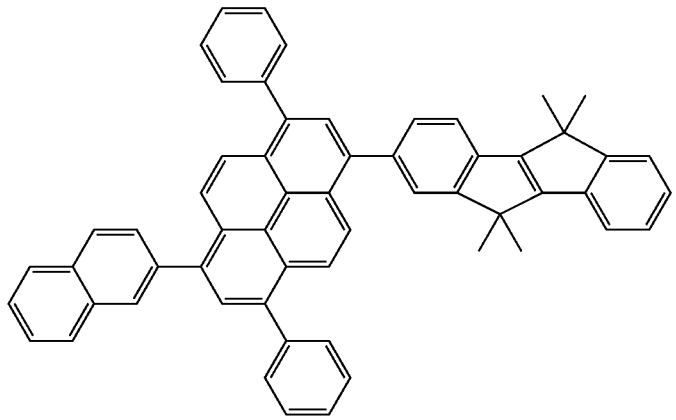

AN-38

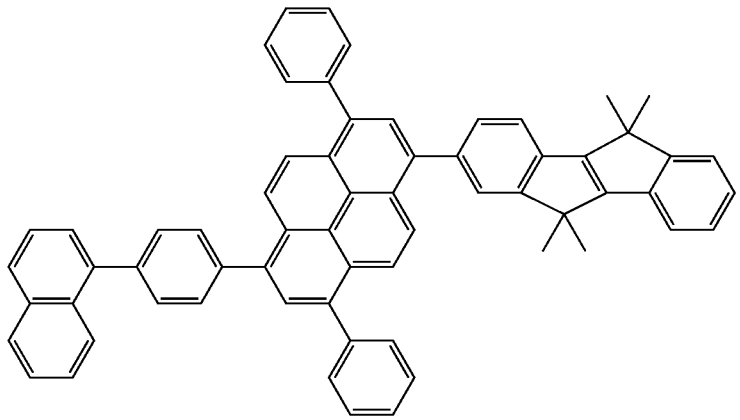

A preparation method of the asymmetric pyrene derivatives of the present invention is explained as follows:

The asymmetric pyrene derivatives represented by the general formula (1) to (3) of the present invention and precursors thereof may be obtained by using a pyrene halide compound and an aryl-boronic acid compound, or an aryl-halide compound and pyrenyl-boronic acid compound as a starting material and applying methods such as Suzuki-coupling reaction and the like. In addition, a combination of a halogenation reaction, an esterification by boric acid and Suzuki-coupling reaction is applied to the precursor as appropriated, and then, the asymmetric pyrene derivatives represented by the general formula (1) to (3) are obtained.

So far, many reports on Suzuki-coupling reaction have been published (Chem. Rev. Vol. 954, No. 7, 2457 (1995), etc.), therefore, it may be carried out in the reaction conditions described therein. The reaction is carried out generally at normal pressure in inert gas atmosphere such as nitrogen, argon, helium and the like, and also under pressurized condition as appropriated. The reaction temperature is in the range of from 15 to 300° C. preferably from 30 to 200° C.

The reaction solvent includes water, aromatic hydrocarbons such as benzene, toluene and xylene, ether such as 1,2-dimethoxyethane, diethyl-ether, methyl-t-butylether, tetrahydrofuran, and dioxane, saturated hydrocarbon such as pentane, hexane, heptane, octane and cyclohexane, halogenated hydrocarbon such as dichloromethane, chloroform, carbon tetrachloride, 1,2-dichloroethane and 1,1,1-trichloroethane, nitrile such as acetonitrile and benzonitrile, ester such as ethylacetate, methylacetate and butylacetate, amide such as N,N-dimethylformamide, N,N-dimethylacetoamide and N-methylpyrrolidone, and the solvent may be used singly or in combination of two or more kind thereof. Among them, toluene, 1,2-dimethoxyethan, dioxane and water are preferred. An amount of the solvent is from 3 to 50 fold by weight, preferably 4 to 20 fold by weight to an aryl-boronic acid and a derivative thereof (or a pyrenyl-boronic acid and a derivative thereof).

A base to be used for the reaction includes, for example, sodium carbonate, potassium carbonate, sodium hydroxide, potassium hydroxide, sodium bicarbonate, potassium bicarbonate, magnesium carbonate, lithium carbonate, potassium fluoride, cesium fluoride, cesium chloride, cesium bromide, cesium carbonate, potassium phosphate, sodium methoxide, potassium t-butoxide, sodium t-butoxide and lithium t-butoxide, and sodium carbonate is preferred. An amount of the base to be used is generally from 0.7 to 10 mole in equivalence, preferably from 0.9 to 6 mole in equivalence to an arylboronic acid and a derivatives thereof (or a pyrenyl-boronic acid and a derivative thereof).

Catalysts to be used for the reaction include, for example, a palladium catalyst such as tetrakis(triphenylphosphine)palladium, dichlorobis(triphenylphosphine)palladium, dichloro[bis(diphenylphosphine) ethane]palladium, dichloro[bis(diphenylphosphine)propane]palladium, dichloro[bis(diphenylphosphine)butane]palladium, dichloro[bis(diphenylphosphine) ferrocene]palladium, and a nickel catalyst such as tetrakis(triphenylphosphine) nickel, dichlorobis(triphenylphosphine)nickel, dichloro[bis(diphenylphosphine) ethane]nickel, dichloro[bis(diphenylphosphine)propane]nickel,dichloro[bis (diphenylphosphine) butane]nickel, dichloro[bis(diphenylphosphine)ferrocene] nickel. The tetrakis(triphenylphosphine)palladium is preferred. An amount of the catalysts to be used is generally from 0.001 to 1 mole in equivalence, preferably from 0.01 to 0.1 mole in equivalence to an anthracene derivative halide.

Halogen of pyrene halide compounds and aryl halide compounds includes iodine atom, bromine atom, chlorine atom and so forth, and iodine atom and bromine atom are preferred.

Although a halogenation reagent for halogenation is not limited, for example, N-succinic acid imide halide is in particular preferably to be used. An amount of the halogenation reagent to be used is generally from 0.8 to 10 mole in equivalence, preferably from 1 to 5 mole in equivalence to a base material.

The reaction is carried out generally in an inert solvent under inert atmosphere such as nitrogen, argon, helium. The inert solvents to be used include N,N-dimethylformamide, N,N-dimethylacetamide, N-methylpyrrolidone, dimethyl sulfoxide, carbon tetrachloride, chlorobenzene, dichlorobenzene, nitrobenzene, toluene, xylene methyl cellosolve, ethyl cellosolve, water and the like, and N,N-dimethylformamide and N-methylpyrrolidone are preferred. An amount of the solvent to be used is generally from 3 to 50 fold by weight, preferably from 5 to 20 fold by weight to a base material. The reaction temperature is generally from 0 to 200° C., preferably from 20 to 120° C.

The esterification by boric acid may be carried out in accordance with known methods (Japan Chemical Society' editorial, The Experimental Chemistry Course No. 4 edition, Vol 24, 61-90; J. Org. Chem., Vol. 60, 7508, etc.). For example, by way of lithiation or Grignard reaction of an arylhalide compound (or a pyrenylhalide compound), the esterification by boric acid is carried out generally under inert atmosphere such as nitrogen, argon, helium and by using an inert solvent as a reaction solvent. The solvents include, for example, saturated hydrocarbon such as pentane, hexane, heptane, octane and cyclohexane, ether such as 1,2-dimethoxyethane, diethylether, methyl-t-butylether, tetrahydrofuran and dioxane, aromatic hydrocarbon such as benzene, toluene and xylene. These may be used singly or as mixture thereof, and dimethylether and toluene are preferred. An amount of the solvent to be used is generally from 3 to 50 fold by weight, preferably from 4 to 20 fold by weight to an arylhalide compound.

The lithiation reagent to be used includes, for example, alkyl metal reagent such as n-butyllithium, t-butyllithium, phenyllithium and methyllithium, amido-base such as lithium di-isopropylamide and lithiumbistrimethylsilylamide, and n-butyllithium is preferred. Further, Grignard reagent may be prepared by reacting an arylhalide compound (or a pyrenylhalide compound) and a magnesium metal. Trialkyl borate to be used includes trimethyl borate, triethyl borate, tri-isopropyl borate, tri-isobutyl borate and the like, and trimethyl borate and tri-isopropyl borate are preferred.

Each amount of the lithiation reagent and the magnesium metal to be used is generally from 1 to 10 mole in equivalence, preferably from 1 to 2 mole in equivalence respectively to an arylhalide compound (or a pyrenylhalide compound). An amount of trialkyl borate to be used is generally from 1 to 10 mole in equivalence, preferably from 1 to 5 mole in equivalence to an arylhalide compound (or a pyrenylhalide compound). The reaction temperature is from −100 to 50° C., in particular preferably from −75 to 10° C.

The asymmetric pyrene derivatives of the present invention are preferred for a light emitting material of the organic EL device, and particularly preferred for a host material of the organic EL device.

An organic EL device of the present invention comprises at least one organic thin film layer including a light emitting layer sandwiched between a pair of electrode consisting of an anode and a cathode, wherein the organic thin film layer comprises at least one kind selected from the asymmetric pyrene derivatives represented by the aforementioned general formulae (1) to (3) singly or as a component of mixture thereof.

In addition, the organic EL device of the present invention is preferred when the aforementioned light emitting layer comprises further an arylamine compound and/or a styrylamine compound.

The preferred styrylamine compounds are shown by the following general formula (4):

(4)

In the general formula (4), Ar2 represents a group selected from among a phenyl group, a biphenyl group, a terphenyl group, a stilbene group and a distyryl aryl group; Ar3 and Ar4 each independently represents a hydrogen atom or an aromatic group having 6 to 20 carbon atoms; further Ar2, Ar3 and Ar4 each may be substituted; p represents an integer of 1 to 4; and more preferably, at least one of Ar3 and Ar4 is substituted with a styryl group.

In the preceding description, the aromatic group having 6 to 20 carbon atoms includes a phenyl group, a naphthyl group, an anthranyl group, a phenanthryl group, a terphenyl group or the like.

The preferred arylamine compounds are represented by the general formula (5):

(5)

In the general formula (5), Ar5 to Ar7 each independently represents an aryl group having 5 to 40 ring carbon atoms that may be substituted, and q represents an integer of 1 to 4.

In the preceding description, the aryl group having 5 to 40 ring carbon atoms includes a phenyl group, a naphthyl group, chrysenyl group, a naphthacenyl group, an anthranil group, a phenanthryl group, a pyrenyl group, a coronyl group, a biphenyl group, a terphenyl group, a pyrrolyl group, a furanyl group, a thiophenyl group, a benz thiophenyl group, an oxadiazolyl group, a diphenyl anthranil group, an indolyl group, a carbazolyl group, a pyridyl group, a benz quinolyl group, a fluoranthenyl group, an acenaphthofluoranthenyl group, a stilbene group or so. Additionally, the aryl group having 5 to 40 carbon atoms may be further substituted with a substituent, and preferable examples of the substituent include an alkyl group having 1 to 6 carbon atoms (an ethyl group, a methyl group, an i-propyl group, a n-propyl group, a s-butyl group, a t-butyl group, a pentyl group, a hexyl group, a cyclopentyl group, a cyclohexyl group, etc.), an alkoxy group having 1 to 6 carbon atoms (an ethoxy group, a methoxy group, an i-propoxy group, a n-propoxy group, a s-butoxy group, a t-butoxy group, a pentoxy group, a hexyloxy group, a cyclo pentoxy group, a cyclohexyl oxy group, etc.), an aryl group having 5 to 40 ring atoms, an amino group substituted with an aryl group having 5 to 40 ring atoms, an ester group which has an aryl group having 5 to 40 ring atoms, an ester group which has an alkyl group having 1 to 6 carbon atoms, a cyano group, a nitro group, a halogen atom and the like.

The following is a description or the construction of the organic EL device of the present invention. Typical examples of the construction of the organic EL device of the present invention include:

(1) an anode/a light emitting layer/a cathode;
(2) an anode/a hole injecting layer/a light emitting layer/a cathode;
(3) an anode/a light emitting layer/an electron injecting layer/a cathode;
(4) an anode/a hole injecting layer/a light emitting layer/an electron injecting layer/a cathode;
(5) an anode/an organic semiconductor layer/a light emitting layer/a cathode;
(6) an anode/an organic semiconductor layer/an electron barrier layer/a light emitting layer/a cathode;
(7) an anode/an organic semiconductor layer/a light emitting layer/an adhesion improving layer/a cathode;
(8) an anode/a hole injecting layer/a hole transporting layer/a light emitting layer/an electron injecting layer/a cathode;
(9) an anode/an insulating layer/a light emitting layer/an insulating layer/a cathode;
(10) an anode/an inorganic semiconductor layer/an insulating layer/a light emitting layer/an insulating layer/a cathode;
(11) an anode/an organic semiconductor layer/an insulating layer/a light emitting layer/an insulating layer/a cathode;
(12) an anode/an insulating layer/a hole injecting layer/a hole transporting layer/a light emitting layer/an insulating layer/a cathode; and
(13) an anode/an insulating layer/a hole injecting layer/a hole transporting layer/a light emitting layer/an electron injecting layer/a cathode.

Among those, the construction (8) is generally employed in particular; however, the construction of the organic EL device is not limited to those shown above as the examples.

In addition, although the asymmetric pyrene derivatives of the present invention may be employed for any of the above organic layers, it is preferable that it is contained in a light emitting zone or a hole transporting zone among those construction elements, and an amount to be contained therein may be selected from in the range of from 30 to 100 mole %.

In general, the organic EL device is produced on a substrate which transmits light. It is preferable that the substrate which transmits light has a transmittance of light of 50% or greater in the visible region of 400 to 700 nm. It is also preferable that a flat and smooth substrate is employed. As the substrate which transmits light, for example, glass sheet and synthetic resin sheet are advantageously employed.

Specific examples of the glass sheet include soda ash glass, glass containing barium and strontium, lead glass, aluminosilicate glass, borosilicate glass, barium borosilicate glass and quartz. In addition, specific examples of the synthetic resin sheet include sheet made of polycarbonate resins, acrylic resins, polyethylene terephthalate resins, polyether sulfide resins and polysulfone resins.

The anode in the organic EL device of the present invention covers a role of injecting holes into a hole transport layer or into a light emitting layer, and it is effective that the anode has a work function of 4.5 eV or greater. Specific examples of the material for the anode include indium tin oxide alloy (ITO), tin oxide (NESA), gold, silver, platinum, copper, etc. With regard to the cathode, its material preferably has a small work function with the aim of injecting electrons into an electron transport layer or into a light emitting layer. The anode can be prepared by forming a thin film of the electrode material described above in accordance with a process such as a vapor deposition process or a sputtering process.

When the light emitted from the light emitting layer is observed through the anode, it is preferable that the anode has a transmittance of the emitted light greater than 10%. It is also preferable that the sheet resistivity of the anode is several hundred $\Omega/\square$ or smaller. The thickness of the anode is, in general, selected in the range of from 10 nm to 1 μm and preferably in the range of from 10 to 200 nm.

In the organic EL device of the present invention, the light emitting layer has the following functions:

(1) The injecting function: the function of injecting holes from the anode or the hole injecting layer and injecting electrons from the cathode or the electron injecting layer when an electric field is applied;

(2) The transporting function: the function of transporting injected charges (electrons and holes) by the force of the electric field; and (3) The light emitting function: the function of providing the field for recombination of electrons and holes and leading the recombination to the emission of light.

As the process for forming the light emitting layer, a well known process such as the vapor deposition process, the spin coating process and the LB process can be employed. It is preferable that a light emitting layer is a molecular sedimentation film particularly. Here, the molecular sedimentation film is defined as a thin film formed by sedimentation of a gas phase material compound or a thin film formed by condensation of a liquid phase material compound. The molecular sedimentation film may be differentiated from a thin film (a molecular build-up film) formed by the LB process, based on the differences between agglomeration structures and higher-order structures, and also the differences resulting from functionalities thereof.

In addition, as shown in Japanese Patent Application Laid-open No. Showa57 (1982)-51781, to form a light emitting layer, a thin film may be formed in accordance with the spin coating and the like of the solution to be prepared by dissolving a binder such as resin and a material compound in solvent.

In the present invention, any well known light emitting material other than a light emitting material consisting of an asymmetric pyrene derivative of the present invention may be optionally contained in the light emitting layer; or a light emitting layer containing other well known light emitting layer may be laminated with the light emitting layer comprising the light emitting material of the present invention each in an extent of not obstructing to achieve the objective of the present invention respectively.

In the present invention, the hole injecting layer and the hole transporting layer are layers which assist injection of holes into the light emitting layer and transport the holes to the light emitting zone. The layers exhibit a great mobility of holes and, in general, have an ionization energy as small as 5.5 eV or smaller. For the hole injecting layer and the hole transporting layer, a material which transports holes to the light emitting layer at a small strength of the electric field is preferable. A material which exhibits, for example, a mobility of holes of at least $10^{-4}$ cm2/V·sec under application of an electric field of from $10^4$ to $10^6$ V/cm is preferable. As for such material, any arbitrary material selected from conventional material commonly used as a charge transporting material for the holes in photoconduction materials and well known material employed for the hole injecting layer in the EL device is usable.

Further examples include triazole derivatives (refer to U.S. Pat. No. 3,112,197, etc.), oxadiazole derivatives (refer to U.S. Pat. No. 3,189,447, etc.), imidazole derivatives (refer to Japanese Examined Patent KOKOKU No. Shou 37-16096, etc.), polyarylalkane derivatives (refer to U.S. Pat. Nos. 3,615,402, 3,820,989 and 3,542,544, Japanese Examined Patent KOKOKU Nos. Shou 45-555 and Shou 51-10983, Japanese Unexamined Patent Application Laid-Open Nos. Shou 51-93224, Shou 55-17105, Shou 56-4148, Shou 55-108667, Shou 55-156953, Shou 56-36656, etc.), pyrazoline derivatives and pyrazolone derivatives (refer to U.S. Pat. Nos. 3,180,729 and 4,278,746, Japanese Unexamined Application Patent Laid-Open Nos. Shou 55-88064, Shou 55-88065, Shou 49-105537, Shou 55-51086, Shou 56-80051, Shou 56-88141, Shou 57-45545, Shou 54-112637, Shou 55-74546, etc.), phenylenediamine derivatives (refer to U.S. Pat. No. 3,615,404, Japanese Examined Patent KOKOKU Nos. Shou 51-10105, Shou 46-3712 and Shou 47-25336, Japanese Unexamined Patent Application Laid-Open Nos. Shou 54-53435, Shou 54-110536, Shou 54-119925, etc.), arylamine derivatives (refer to U.S. Pat. Nos. 3,567,450, 3,180, 703, 3,240,597, 3,658,520, 4,232,103, 4,175,961 and 4,012, 376, Japanese Examined Patent KOKOKU Nos. Shou 49-35702 and Shou 39-27577, Japanese Unexamined Patent Application Laid-Open Nos. Shou 55-144250, Shou 56-119132 and Shou 56-22437, West German Patent No. 1,110,518, etc.), chalcone derivatives which is substituted with amino group (refer to U.S. Pat. No. 3,526,501, etc.), oxazole derivatives (disclosed in U.S. Pat. No. 3,257,203, etc.), styryl anthracene derivatives (refer to Japanese Unexamined Patent Application Laid-Open No. Shou 56-46234, etc.), fluorenone derivatives (refer to Japanese Unexamined Patent Application Laid-Open No. Shou 54-110837, etc.), hydrazone derivatives (refer to U.S. Pat. No. 3,717,462, Japanese Unexamined Patent Application Laid-Open Nos. Shou 54-59143, Shou 55-52063, Shou 55-52064, Shou 55-46760, Shou 55-85495, Shou 57-11350, Shou 57-148749, Hei 2-311591, etc.), stilbene derivatives (refer to Japanese Unexamined Patent Application Laid-Open Nos. Shou 61-210363, Shou 61-228451, Shou 61-14642, Shou 61-72255, Shou 62-47646, Shou 62-36674, Shou 62-10652, Shou 62-30255, Shou 60-93455, Shou 60-94462, Shou 60-174749, Shou 60-175052, etc.), silazane derivatives (U.S. Pat. No. 4,950, 950), polysilane-based copolymers (Japanese Unexamined Patent Application Laid-Open No. Hei 2-204996), aniline-based copolymers (Japanese Unexamined Patent Application Laid-Open No. Hei 2-282263), an electroconductive polymer oligomer which is disclosed in Japanese Unexamined Patent Application Laid-Open No Hei 1-211399 (particularly, thiophene oligomer), etc.

With regard to the material of the hole injecting layer, the above materials are also employable, however, porphyrin compounds, aromatic tertiary amine compounds and styryl amine compounds (refer to U.S. Pat. No. 4,127,412, Japanese Unexamined Patent Application Laid-Open Nos. Shou 53-27033, Shou 54-58445, Shou 54-149634, Shou 54-64299, Shou 55-79450, Shou 55-144250, Shou 56-119132, Shou 61-295558, Shou 61-98353, Shou 63-295695, etc.) are preferable and the aromatic tertiary amine compounds are particularly preferable.

Further examples include, for example, 4,4'-bis(N-(1-naphthyl) —N-phenylamino)biphenyl (abbreviated as NPD hereunder) having 2 fused aromatic rings in its molecular described in U.S. Pat. Nos. 5,061,569, 4,4',4"-tris (N-(3-methylphenyl)-N-phenylamino) triphenyl amine (abbreviated as MTDATA hereunder) made by connecting three triphenyl amine units to form a star burst type, etc.

Further, in addition to the aforementioned asymmetric pyrene derivatives as a material for the light emitting layer, inorganic compound such as p-type silicon, p-type silicon carbide or so is employable as the material for the hole injecting layer.

To form the hole injecting layer or the hole transporting layer, a thin film may be formed from the material for the hole injecting layer or the hole transporting layer, respectively, in accordance with a well known process such as the vacuum vapor deposition process, the spin coating process, the casting process and the LB process. Although the thickness of the hole injecting layer and the hole transporting layer is not particularly limited, the thickness is usually from 5 nm to 5 μm.

In the organic EL device of the present invention, the organic semiconductor layer assists to inject the holes or to inject the electrons into the light emitting layer, and it is preferable for the organic semiconductor layer to have a electric conductivity of $10^{-10}$ S/cm or greater. With regard to a material for the organic semiconductor layer, electroconductive oligomers such as an oligomer having thiophene, an oligomer having arylamine disclosed in Japanese Patent Application Laid-Open No. Heisei 8 (1996)-193191 and so on, electroconductive dendrimers such as a dendrimer having an arylamine and so on are employable.

The electron injection layer in the organic EL device of the present invention is a layer which assists injection of electrons into the light emitting layer and exhibits a great mobility of electrons. Among the electron injecting layers, an adhesion improving layer is a layer made of a material exhibiting excellent adhesion with the cathode.

Further, it has been known that interference between luminescence directly coming from an anode and luminescence coming through reflection by an electrode is caused since a light emitted in an organic EL device is reflected by an electrode (in this case, a cathode). In order to utilize the interference effect efficiently, a thickness of an electron transferring layer is selected from the range of several nm to several μ m accordingly. It is preferable that an electron mobility is at least $10^{-5}$ cm2/Vs or more when an electric field of from $10^4$ to $10^6$V/cm is applied.

As the material for the electron injecting layer, 8-hydroxyquinoline, metal complexes of derivatives thereof and oxadiazole derivatives are preferable.

Examples of the 8-hydroxyquinoline and metal complexes of derivatives thereof include metal chelates of oxinoid compounds including chelates of oxine (in general, 8-quinolinol or 8-hydroxyquinoline). For example, tris(8-quinolinol)aluminum (Alq) can be employed as the electron injecting material.

Further, examples of the oxadiazole deliveries include an electron transfer compound shown as the following general formulae:

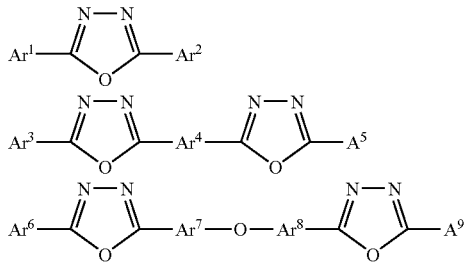

wherein Ar1, Ar2, Ar3, Ar5, Ar6 and Ar9 each independently represents a substituted or unsubstituted aryl group, which may be the same with or different from each other; Ar4, Ar7 and Ar8 each independently represents a substituted or unsubstituted arylene group, which may be the same with or different from each other.

Examples of the aryl group include a phenyl group, a biphenyl group, an anthranil group, a perilenyl group and a pyrenyl group. Further, examples of the arylene group include a phenylene group, a naphthylene group, a biphenylene group, an anthranylene group, a perilenylene group, a pyrenylene group, etc. Furthermore, examples of the substituent include an alkyl group having 1 to 10 carbon atoms, an alkoxy group or a cyano group each having 1 to 10 carbon atoms respectively, etc. With regard to the electron transfer compound, those compounds having a thin film forming capability are preferable.

Specific examples of the electron transfer compounds are shown below:

In addition, a material to be used for an electron injecting layer and an electron transferring layer includes any of compounds represented by the following general formulae (A) to (G).

A nitrogen-containing heterocyclic derivative represented by a following general formula (A) or a following general formula (B):

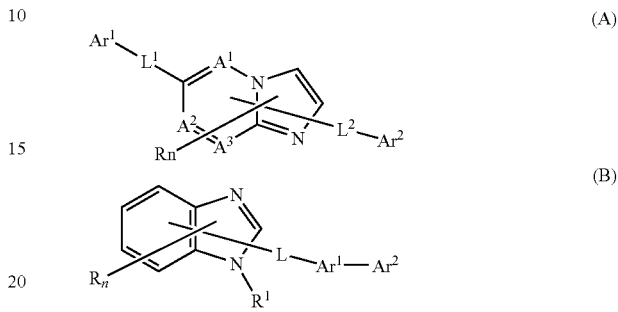

In the general formulae (A) and (B), A1 to A3 each independently represents nitrogen atom or carbon atom.

Ar1 represents a substituted or unsubstituted aryl group having 6 to 60 ring carbon atoms, or a substituted or unsubstituted hetero aryl group having 3 to 60 ring carbon atoms, Ar2 represents a hydrogen atom, a substituted or unsubstituted aryl group having 6 to 60 ring carbon atoms, or a substituted or unsubstituted hetero aryl group having 3 to 60 ring carbon atoms, a substituted or unsubstituted alkyl group having 1 to 20 carbon atoms, or a substituted or unsubstituted alkoxy group having 1 to 20 carbon atoms, or a bivalent group of these; Either Ar1 or Ar2 is, however, a substituted or unsubstituted condensed ring group having 10 to 60 ring carbon atoms or a substituted or unsubstituted monohetero condensed ring group having 3 to 60 ring carbon atoms.

L1, L2 and L each independently represents a single bond, a substituted or unsubstituted arylene group having 6 to 60 ring carbon atoms, a substituted or unsubstituted hetero

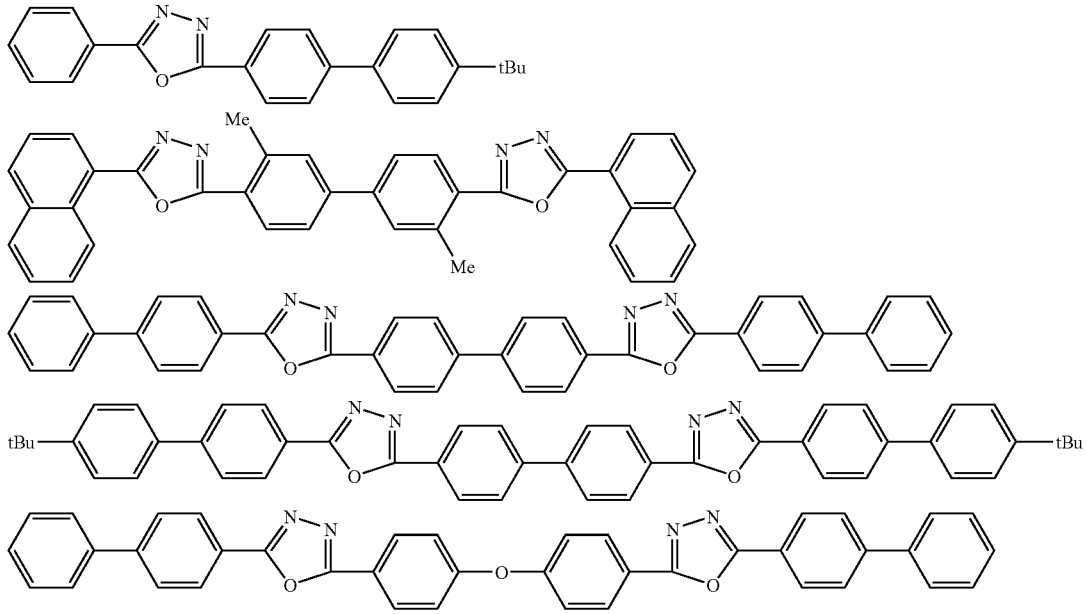

arylene group having 3 to 60 ring carbon atoms, or a substituted or unsubstituted fluorene group.

R represents hydrogen, a substituted or unsubstituted aryl group having 6 to 60 ring carbon atoms, or a substituted or unsubstituted hetero aryl group having 3 to 60 ring carbon atoms, a substituted or unsubstituted alkyl group having 1 to 20 carbon atoms, or a substituted or unsubstituted alkoxy group having 1 to 20 carbon atoms. n represents an integer of from 0 to 5, a plural number of R, if any, may be either the same with or different from each other when n is 2. Further, a plural number of R, if any, when these are adjacent to each other, may be bonded each other to form a carbocyclic aliphatic ring or a carbocyclic aromatic ring.

A nitrogen-containing heterocyclic derivative represented by a following general formula (C):

In the general formula (C), HAr represents a nitrogen-containing heterocyclic derivative and further may have a substituent, having 3 to 40 of carbon atoms, L represents a single bond, an arylene group and further may have a substituent, having 6 to 60 carbon atoms, a hetero arylene group and further may have a substituent, having 3 to 60 carbon atoms, or a fluorene group and further may have substituent, Ar1 represents a bivalent aromatic hydrocarbon group and further may have a substituent, having 6 to 60 carbon atoms, Ar2 represents an aryl group and further may have a substituent, having 6 to 60 carbon atoms or a hetero aryl group and further may have a substituent, having 3 to 60 carbon atoms, represents a nitrogen-containing heterocyclic derivative.

A silacyclopentadiene derivative represented by a following general formula (D):

In the general formula (D), X and Y each independently represents a substituted or unsubstituted hydrocarbon group having 1 to 6 of carbon atoms, an alkoxy group, an alkenyloxy group, an alkynyloxy group, a hydroxyl group, a substituted or unsubstituted aryl group, a substituted or unsubstituted hetero ring, or a structure forming a saturated or unsaturated ring by bonding X and Y, of R1 to R4 each represents independently a hydrogen atom, a halogen atom, a substituted or unsubstituted alkyl group having 1 to 6 carbon atoms, an alkoxy group, an aryloxy group, a perfuluoroalkyl group, a perfuluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfunyl group, a sulfonyl group, a silyl group, a carbamoyl group, an aryl group, a heterocyclic group, an alkenyl group, a nitro group, a formyl group, a nitroso group, a formyloxy group, an isocyano group, a cyanate group, a thiosyanate group, an isothiosyanate group or a cyano group, or a substituted or unsubstituted condensed ring structure when these are adjacent to each other.

A borane derivative represented by a following general formula (E):

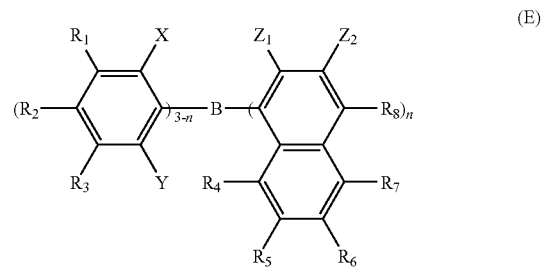

In the general formula (E), R1 to R8 and Z2 each independently represents a hydrogen atom, a saturated or unsaturated hydrocarbon, an aromatic group, an heterocyclic group, a substituted amino group, a substituted boryl group, an alkoxy group or an aryloxy group, each of X, Y and Z1 represents independently a saturated or unsaturated hydrocarbon, an aromatic group, an heterocyclic group, a substituted amino group, an alkoxy group or an aryloxy group, and substitutes of Z1 and Z2 may bond each other to form a condensed ring, n represents an integer of 1 to 3, Z1 may be different from each other when n is 2 or more; any compound, however, of which n is 1, X, Y and R2 are methyl groups, and R8 is a hydrogen atom or a substituted boryl group, or, of which n is 3 and Z1 is a methyl group, is excluded.

In the general formula (F), Q1 and Q2 each independently represents a ligand shown by the general formula (G), L represents a ligand shown by a halogen atom, a substituted or unsubstituted alkyl group, a substituted or unsubstituted cycloalkyl group, a substituted or unsubstituted aryl group, heterocyclic group, —OR1 (R1 represents a hydrogen atom, a substituted or unsubstituted alkyl group, a substituted or unsubstituted cycloalkyl group, a substituted or unsubstituted aryl group, or a substituted or unsubstituted heterocyclic group or —O—Ga-Q3 (Q4) (Q3 and Q4 are the same with Q1 and Q2).

In the general formula (G), rings $A^1$ and $A^2$ have a six-member aryl-ring structure and further may have a substituent, formed by condensing each other.

The metal complex shows a strong property as a n-type impurity semiconductor so that a capability of electron injection is significant. In addition, affinity between the metal complex formed and the ligand is strong so that fluorescent quantum efficiency for a light emitting material is increased.

The specific examples of a substituent for $A^1$ and $A^2$ forming a ligand of the general formula (G) include a halogen atom of halogen, bromine and iodine, a substituted or unsubstituted alkyl group such as a methyl group, a ethyl group, a propyl group, a butyl group, a sec-butyl group, a tert-butyl group, a pentyl group, a hexyl group, a heptyl group, an octyl group, a stearyl group and trichloromethyl group, a substituted or unsubstituted aryl group such as a phenyl group, a naphtyl group, a 3-methynaphtyl group, a 3-methoxynaphtyl group, a 3-fluorophenyl group, a 3-trichloromethylphenyl group, a 3-trifluoromethylphenyl group, and a 3-nitrophenyl group, a substituted or unsubstituted alkoxy group such as a methoxy group, a n-butoxy group, a tert-butoxy group, a trichloromethoxy group, a trifluoroethoxy group, a pentafluoroporopoxy group, a 2,2,3,3-tetra fluoroporopoxy group, a 1,1,1,3,3,3-hexafluoro-2-propoxy group, a 6-(perfluoroethyl)hexyloxy group, a substituted or unsubstituted aryloxy group such as a phenoxy group, a p-nitrophenoxy group, a p-tert-butylphenoxy group, a 3-fluorophenoxy group, a pentafluorophenoxy group, and a 3-trifluoromethylphenoxy group, a substituted or unsubstituted alkylthio group such as a methylthio group, an ethylthio group, a tert-butykthio group, a hexylthio group, an octylthio group and a trifluoromethylthio group, a substituted or unsubstituted arylthio group such as a phenylthio group, a p-nitrophenylthio group, a p-tert-butylphenylthio group, a 3-fluorophenylthio group, pentafluorophenylthio group and 3-trifluoromethylphenylthio group, a cyano group, a nitro group, an amino group, a mono or di substituted amino group such as a methyamino group, a dimethylamino group, a ethylamino group, a diethylamino group, a dipropylamino group, a dibutylamino group and a diphenylamino group, an acylamino group such as a bis(acetoxymethyl)amino group, a bis(acetoxyethyl) amino group, a bis(acetoxypropyl)amino group and bis(acetoxybutyl)amino group, a hydroxy group, a siloxy group, an acyl group, a carbamoyl group such as a methylcarbamoyl group, dimethylcarbamoyl group, an ethylcarbamoyl group, a diethylcarbamoyl group, a propylcarbamoyl group, a butylcarbamoyl group and phenylcarbamoyl group, a carboxylic acid group, a sulfonic acid group, an imido group, a cycloalkyl group such as a cyclopentane group and a cyclohexyl group, an aryl group such as a phenyl group, a naphthyl group, a biphenyl group, an anthranyl group, a phenanthryl group, a fluorenyl group and a pyrenyl group, and a heterocyclic group such as a pyridinyl group, a pyrazinyl group, a pyrimidyl group, a pyridazinyl group, a triazinyl group, an indolinyl group, a quinolinyl group, an acridinyl group, a pyrrolidyl group, a dioxanyl group, a morpholizinyl group, a piperazinyl group, a triatinyl group, a carbazolyl group, a furanyl group, a thiophenyl group, an oxazolyl group, an oxadiazolyl group, a benzoxazolyl group, a thiazolyl group, a thiadiazolyl group, a benzothiazolyl group, a triazolyl group, an imidazolyl group, a benzoimidazolyl group and a pranyl group. In addition, the above substituent may bond each other to further form a six-member aryl ring or a hetero-ring.

In the present invention, it is preferable that a reductive dopant is added in either the electron transporting zone or an interfacial zone between the cathode and the organic layer. The reductive dopant used in the present invention is defined as a substance which reduces the electron transporting compound. Examples of the reductive dopant include at least one compound selected from alkali metals, alkali metallic complexes, alkali metal compounds, alkaline earth metals, alkaline earth metallic complexes, alkaline earth metal compounds, rare earth metals, rare earth metallic complexes and rare earth metal compounds.

Examples of the preferable reductive dopant include at least one alkali metal selected from a group consisting of Li (the work function: 2.93 ev), Na (the work function: 2.36 eV), K (the work function: 2.28 eV), Rb (the work function: 2.16 eV) and Cs (the work function: 1.95 eV) or at least one alkaline earth metals selected from a group consisting of Ca (the work function: 2.9 eV), Sr (the work function: 2.0 to 2.5 eV) and Ba (the work function: 2.52 eV); whose work function of 2.9 eV or smaller is particularly preferable. Among the above, the preferable reductive dopant include at least one alkali metal selected from a group consisting of K, Rb and Cs, the more preferred is Rb or Cs, and the most preferred is Cs. These alkali metals have particularly high ability of reduction so that improvement of an emission luminance and longer lasting of a lifetime of the organic EL device may be realized. In addition, a combination of two or more of alkali metals is also preferable as a reductive dopant having 2.9 eV or less of the work function. In particular, a combination of Cs, for example with Na, Cs, K or Rb, or Na and K is preferable. By combing and containing Cs therein, the reduction ability can be demonstrated effectively, and improvement of an emission luminance and longer lasting of a lifetime of the organic EL device may be realized by adding it into an electron injecting zone.

In the organic EL device of the present invention, an electron injecting layer formed with an insulating material or a semiconductor may be further sandwiched between the cathode and the organic thin film layer. The electron injecting layer effectively prevents leak in the electric current and improves the electron injecting capability. It is preferable that at least one metal compound selected from the group consisting of alkali metal chalcogenides, alkaline earth metal chalcogenides, alkali metal halides and alkaline earth metal halides is used as the insulating material. It is preferable that the electron injecting layer is constituted with the above alkali metal chalcogenide since the electron injecting property can be improved. Preferable examples of the alkali metal chalcogenide include $Li_2O$, LiO, $Na_2S$, $Na_2Se$ and NaO. Preferable examples of the alkaline earth metal chalcogenide include CaO, BaO, SrO, BeO, BaS and CaSe. Preferable examples of the alkali metal halide include LiF, NaF, KF, LiCl, KCl and NaCl. Preferable examples of the alkaline earth metal halide include fluorides such as $CaF_2$, $BaF_2$, $SrF_2$, $MgF_2$ and $BeF_2$ and halides other than the fluorides.

Examples of the semiconductor constituting the electron transporting layer include oxides, nitrides and nitriding oxides containing at least one element selected from Ba, Ca, Sr, Yb, Al, Ga, In, Li, Na, Cd, Mg, Si, Ta, Sb and Zn, which are used singly or in combination of two or more. It is preferable that the inorganic compound constituting the electron transporting layer is in the form of a fine crystalline or amorphous insulating thin film When the electron transporting layer is constituted with the above insulating thin film, a more uniform thin film can be formed and defective pixels such as dark spots can be decreased. Examples of the inorganic compound include the alkali metal chalcogenides, the alkaline earth metal chalcogenides, the alkali metal halides and the alkaline earth metal halides which are described above.

As the cathode for the organic EL device of the present invention, an electrode substance such as metal, alloy, electroconductive compound and those mixture having a small work function (4 eV or smaller) is employed. Examples of the electrode substance include potassium, sodium-potassium alloy, magnesium, lithium, magnesium-silver alloy, aluminum/aluminum oxide, aluminum-lithium alloy, indium, rare earth metal, etc.

The cathode can be prepared by forming a thin film of the electrode material described above in accordance with a process such as the vapor deposition process and the sputtering process.

When the light emitted from the light emitting layer is observed through the cathode, it is preferable that the cathode has a transmittance of the emitted light greater than 10%. It is also preferable that the sheet resistivity of the cathode is several hundred Ω/□ or smaller. The thickness of the cathode is, in general, selected in the range of from 10 nm to 1 μm and preferably in the range of from 50 to 200 nm.

In general, an organic EL device tends to form defects in pixels due to leak and short circuit since an electric field is applied to ultra-thin films. To prevent the formation of the defects, a layer of an insulating thin film may be inserted between the pair of electrodes.

Examples of the material employed for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide. Mixtures and laminates of the above compounds can also be employed.

To produce an organic EL device of the present invention, for example, a cathode, a light emitting layer and, where necessary, a hole injecting layer and an electron injecting layer are formed in accordance with the aforementioned process using the aforementioned materials, and the anode is formed in the last step. An organic EL device may be produced by forming the aforementioned layers in the order reverse to that described above, i.e., an anode being formed in the first step and a cathode in the last step.

An embodiment of the process for producing an organic EL device having a construction in which a cathode, a hole injecting layer, a light emitting layer, an electron injecting layer and an anode are disposed sequentially on a light-transmitting substrate will be described in the following.

On a suitable light-transmitting substrate, a thin film made of a material for the cathode is formed in accordance with the vapor deposition process or the sputtering process so that the thickness of the formed thin film is 1 μm or smaller and preferably in the range of 10 to 200 nm. The formed thin film is employed as the cathode. Then, a hole injecting layer is formed on the cathode. The hole injecting layer can be formed in accordance with the vacuum vapor deposition process, the spin coating process, the casting process or the LB process, as described above. The vacuum vapor deposition process is preferable since a uniform film can be easily obtained and the possibility of formation of pin holes is small.

When the hole injecting layer is formed in accordance with the vacuum vapor deposition process, in general, it is preferable that the conditions in general are suitably selected in the following ranges: temperature of the deposition source: 50 to 450° C.; vacuum level: $10^{-7}$ to $10^{-3}$ Torr; deposition rate: 0.01 to 50 nm/second; temperature of the substrate: −50 to 300° C.; and film thickness: 5 nm to 5 μm; although the conditions of the vacuum vapor deposition are different depending on the employed compound (the material for the hole injecting layer) and the crystal structure and the recombination structure of the hole injecting layer to be formed.

Subsequently, the light-emitting layer is formed on the hole-injecting layer formed above. Also the formation of the light emitting layer can be made by forming the light emitting material according to the present invention into a thin film in accordance with the vacuum vapor deposition process, the sputtering process, the spin coating process or the casting process. The vacuum vapor deposition process is preferable because a uniform film can be easily obtained and the possibility of formation of pinholes is small. When the light-emitting layer is formed in accordance with the vacuum vapor deposition process, in general, the conditions of the vacuum vapor deposition process can be selected in the same ranges as those described for the vacuum vapor deposition of the hole-injecting layer although the conditions are different depending on the used compound. It is preferable that the thickness is in the range of from 10 to 40 nm.

Next, the electron-injecting layer is formed on the light-emitting layer formed above. Similarly to the hole injecting layer and the light-emitting layer, it is preferable that the electron-injecting layer is formed in accordance with the vacuum vapor deposition process since a uniform film must be obtained. The conditions of the vacuum vapor deposition can be selected in the same ranges as those for the hole injecting layer and the light-emitting layer.

In the last step, the anode is formed on the electron injecting layer, and an organic EL device can be fabricated. The anode is made of a metal and can be formed in accordance with the vacuum vapor deposition process or the sputtering process.

It is preferable that the vacuum vapor deposition process is employed in order to prevent the lower organic layers from damages during the formation of the film. In the above production of the organic EL device, it is preferable that the above layers from the anode to the cathode are formed successively while the production system is kept in a vacuum after being evacuated.

The process for forming the layers in the organic EL device of the present invention is not particularly limited. A conventional process such as the vacuum vapor deposition process and the spin coating process can be used. The organic thin film layer comprising the compound having a spiro bond represented by the foregoing general formula (1) used in the organic EL device of the present invention can be formed in accordance with the vacuum vapor deposition process, the molecular beam epitaxy process (the MBE process) or, using a solution prepared by dissolving the compound into a solvent, in accordance with a conventional coating process such as the dipping process, the spin coating process, the casting process, the bar coating process and the roller coating process.

The thickness of each layer in the organic thin film layer in the organic EL device of the present invention is not particularly limited, therefore, a thickness within the range of several nanometers to 1 μm is preferable so as to reduce the defects such as pin holes and improve the efficiency.

When a direct voltage is applied on the organic EL device produced in the above manner, when a direct voltage of 5 to 40 V is applied in the condition that the cathode is connected to a positive electrode (+) and the anode is connected to a negative electrode (−), then a light emitting is observed. When the connection is reversed, no electric current is produced and no light is emitted at all. When an alternating voltage is applied on the organic EL device, the uniform light emission is observed only in the condition that the polarity of the cathode is positive and the polarity of the anode is negative. When an alternating voltage is applied on the organic EL device, any type of wave shape can be employed.

EXAMPLE

This invention will be described in further detail with reference to Examples, which does not limit the scope of this invention

Synthesis Example 1

Synthesis of Compound (AN-2)

(1) Synthesis of Intermediate [1-bromo-6-(4-naphthalene-1-yl-phenyl)pyrene]

7.4 g of 4-(naphthalene-1-yl)phenyl boronic acid prepared by a well known method and 7.0 g of conventional 1-bromopyrene were dissolved in 80 ml of dimethoxyethane (DME). Subsequently, 0.58 g of tetrakistriphenylphosphine palladium and 40 ml of 2M-sodium carbonate aqueous solution were added therein, followed by argon displacement. After heating and refluxing over 8 hours, it was stood to cool and then an organic layer was extracted therefrom by toluene. The organic layer was washed by saturated salt water, followed by drying through anhydrous sodium sulfate, and then the organic solvent was removed by an evaporator. The residue was refined through a silica gel chromatography (a developing solvent: toluene) and then 10.0 g of 1-(4-naphthalene-1-yl-phenyl)pyrene was obtained. (yield: 99%)

10.0 g of 1-(4-naphthalene-1-yl-phenyl)pyrene obtained was dispersed into 100 ml of dimethyl formaldehyde (DMF), and 5.3 g N-bromosuccinimide (NBS) in DMF solution was dropped therein at room temperature. After stirred over 5 hours, it was left around overnight. After the overnight, 150 ml of water was added to it and the deposited crystal was filtrated, followed by water and ethanol washing of the crystal. The crystal obtained was refined through a silica gel chromatography (a developing solvent: hexane/toluene=2/1) and then 4.5 g of 1-bromo-6-(4-naphthalene-1-yl-phenyl)pyrene (the yield: 38%) and 3.8 g of 1-bromo-8-(4-naphthalene-1-yl-phenyl)pyrene were obtained (the yield: 32%) as the intermediates.

(2) Synthesis of Compound (AN-2)

2.7 g of (4-naphthalene-2-yl)phenyl boronic acid prepared by a well known method and 4.5 g of 1-bromo-6-(4-naphthalene-1-yl-phenyl)pyrene were dissolved in 40 ml of DME. Subsequently, 0.22 g of tetrakistriphenylphosphine palladium and 15 ml of 2M-sodium carbonate aqueous solution were added therein, followed by argon displacement. After heating and refluxing over 9 hours, it was stood to cool and an organic layer was extracted therefrom by toluene. The organic layer was washed by saturated salt water, followed by drying through anhydrous sodium sulfate, and then the organic solvent was removed by an evaporator. The residue was refined through a silica gel chromatography (a developing solvent: hexane/toluene=1/1) and then 3.1 g of the objective compound (AN-2) was obtained.

The measurement result of the compound by FD-MS (Field Desorption Mass Spectrometry analysis) showed m/z=606 to $C_{48}H_{30}$=606, therefore the objective compound (AN-2) was confirmed (the yield: 54%).

Synthesis Example 2

Synthesis of Compound (AN-7)

2.3 g of 3-(naphthalene-2-yl)phenyl boronic acid prepared by a well known method and 3.8 g of 1-bromo-8-(4-naphthalene-1-yl-phenyl)pyrene were dissolved in 40 ml of DME. Subsequently, 0.19 g of tetrakis(triphenylphosphine)palladium and 13 ml of 2M-sodium carbonate aqueous solution were added therein, followed by argon displacement. After heating and refluxing for 9 hours, it was stood to cool and then an organic layer was extracted therefrom by toluene. The organic layer was washed by saturated salt water, followed by drying through anhydrous sodium sulfate, and then the organic solvent was removed by an evaporator. The residue was refined through a silica gel chromatography (a developing solvent: hexane/toluene=1/1) and then 2.7 g of the objective compound (AN-7) was obtained.

The measurement result of the compound by FD-MS showed m/z=606 to $C_{48}H_{30}$=606, therefore the objective compound (AN-7) was confirmed (the yield: 58%).

Synthesis Example 3

Synthesis of Compound (AN-3)

(1) Synthesis of Intermediate [1-bromo-6-(naphthalene-1-yl)pyrene]

1-naphthalene boronic acid in place of 4-(naphthalene-1-yl)phenyl boronic acid was used in Synthesis Example 1 (1), and then 1-bromo-6-(naphthalene-1-yl)pyrene and 1-bromo-8-(naphthalene-1-yl) pyrene were obtained.

(2) Synthesis of Compound (AN-3)

The procedure of Synthesis Example 1 (2) was repeated except that 4.0 g of 1-bromo-6-(naphthalene-1-yl)pyrene and 1.85 g of 2-naphthalene boronic acid in place of 4-(naphthalene-2-yl)phenyl boronic acid and 1-bromo-6-(4-naphthalene-1-yl-phenyl)pyrene were used, and then 2.7 g of the light-yellow crystalline objective compound (AN-3) was obtained.

The measurement result of the compound by FD-MS showed m/z=454 to $C_{36}H_{22}$=454, therefore the objective compound (AN-3) was confirmed.

Synthesis Example 4

Synthesis of Compound (AN-19)

The procedure of the synthesis example 1 (2) was repeated except that 4.0 g of 1-bromo-8-(naphthalene-1-yl)pyrene obtained in Synthesis Example 3 (1) and 1.85 g of 2-naphthalene boronic acid in place of 4-(naphthalene-2-yl)phenyl boronic acid and 1-bromo-6-(4-naphthalene-1-yl-phenyl) pyrene were used, and then 2.9 g of the light-yellow crystalline objective compound (AN-19) was obtained.

The measurement result of the compound by FD-MS showed m/z=454 to $C_{36}H_{22}$=454, therefore the objective compound (AN-19) was confirmed.

Synthesis Example 5

Synthesis of Compound (AN-20)

5.0 g of the compound (AN-3) was dispersed in 50 ml of DMF and 4.0 g of NBS in DMF solution was dropped thereto at room temperature. After 3 days reaction, 100 ml of water was added thereto, and the deposited crystal was filtrated, followed by water and ethanol-washing of the crystal. The crystal obtained was refined through a silica gel chromatography (a developing solvent: hexane/toluene=2/1) and then 4.0 g of 1,6-dibromo-3-(naphthalene-2-yl)-8-(naphthalene-1-yl)pyrene was obtained as the intermediate (the yield: 60%).

4.0 g of 1,6-dibromo-3-(naphthalene-2-yl)-8-(naphthalene-1-yl)pyrene obtained and 1.9 g of phenyl boronic acid were dissolved in 60 ml of DME. Subsequently, 0.5 g of tetrakistriphenylphosphinepalladium and 20 ml of 2M-sodium carbonate aqueous solution were added therein, followed by argon displacement. After heating and refluxing over 8 hours, it was stood to cool and then the deposited crystal was filtrated. After washing the crystal by water and methanol, it was refined through a silica gel chromatography (a developing solvent: toluene), and then 2.9 g of the light-yellow crystalline objective compound (AN-20) was obtained.

The measurement result of the compound by FD-MS showed m/z=606 to $C_{48}H_{30}$=606, therefore the objective compound (AN-20) was confirmed (the yield: 73%).

Synthesis Example 6

Synthesis of Compound (AN-21)

(1) Synthesis of Intermediate [1-bromo-3,8-dinaphthalene-2-yl-6-phenylpyrene]

8.0 g of 1,6-dinaphthalene-2-yl-pyrene prepared by a well known method was dispersed into 80 ml of DMF, and 3.2 g of NBS in DMF solution was dropped therein at room temperature. After 3 days reaction, 150 ml of water was added to it and the deposited crystal was filtrated, followed by water and ethanol washing of the crystal. The crystal obtained was refined through a silica gel chromatography (a developing solvent: hexane/toluene=2/1) and then 8.5 g of 3-bromo-1,6-dinaphthalene-2-yl-pyrene was obtained as the intermediate (the yield: 90%). 8.5 g of 3-bromo-1,6-dinaphthalene-2-yl-pyrene obtained and 2.3 g of phenyl boronic acid were dissolved in 100 ml of DME. Subsequently, 0.55 g of tetrakistriphenylphosphinepalladium and 25 ml of 2M-sodium carbonate aqueous solution were added therein, followed by argon displacement. After heating and refluxing over 8 hours, it was stood to cool, and then the deposited crystal was filtrated. After washing the crystal by water and methanol, it was refined through a silica gel chromatography (a developing solvent: toluene), and then 5.4 g of 1,6-dinaphthalene-2-yl-3-phenylpyrene of the light-yellow crystalline was obtained (the yield: 64%).

5.4 g of 1,6-dinaphthalene-2-yl-3-phenylpyrene was dispersed into 60 ml of DMF, and 1.9 g NBS in DMF solution was dropped therein at room temperature. After 3 days reaction, 150 ml of water was added to it and the deposited crystal was filtrated, followed by water and ethanol washing of the crystal.
The crystal obtained was refined through a silica gel chromatography (a developing solvent: hexane/toluene=2/1) and then 5.9 g of 1-bromo-3,8-dinaphthalene-2-yl-6-phenylpyrene was obtained as the intermediate (the yield: 95%).

(2) Synthesis of Compound (AN-21)

5.9 g of 1-bromo-3,8-dinaphthalene-2-yl-6-phenylpyrene obtained and 2.3 g of 2-biphenyl boronic acid were dissolved in 80 ml of DME. Subsequently, 0.35 g of tetrakistriphenylphosphinepalladium and 15 ml of 2M-sodium carbonate aqueous solution were added therein, followed by argon displacement. After heating and refluxing over 7 hours, it was stood to cool and then the deposited crystal was filtrated. After washing the crystal by water and methanol, it was refined through a silica gel chromatography (a developing solvent: toluene), and then 4.8 g of the light-yellow crystalline objective compound (AN-21) was obtained.

The measurement result of the compound by FD-MS showed m/z=682 to $C_{54}H_{34}$=682, therefore the objective compound (AN-21) was confirmed (the yield: 73%).

Synthesis Example 7

Synthesis of Compound (AN-8)

10 g of 2,7-diiodo-9,9'-dimethyl-9H-fluorene prepared by a well known method and 4.6 g of 1-naphthalene boronic acid were dissolved in 150 ml of toluene. Subsequently, 0.78 g of tetrakistriphenylphosphinepalladium and 35 ml of 2M-sodium carbonate aqueous solution were added therein, followed by argon displacement. After heating and refluxing over 8 hours, it was stood to cool and then an organic layer was extracted therefrom by toluene. The organic layer was washed by saturated salt water, followed by drying through anhydrous sodium sulfate, and then the organic solvent was removed by an evaporator. The residue was refined through a silica gel chromatography (a developing solvent: hexane/toluene=1/1) and then 7.1 g of diiodo-9,9'-dimethyl-7-naphthalene-1-yl-9H-fluorene was obtained (the yield: 71%).

7.1 g of diiodo-9,9'-dimethyl-7-naphthalene-1-yl-9H-fluorene obtained and 4.7 g of 1-pyrene boronic acid were dissolved in 100 ml of DME. Subsequently, 0.55 g of tetrakistriphenylphosphinepalladium and 25 ml of 2M-sodium carbonate aqueous solution were added therein, followed by argon displacement. After heating and refluxing over 7 hours, it was stood to cool and then the deposited crystal was filtrated. After washing the crystal by water and methanol, it was refined through a silica gel chromatography (a developing solvent: toluene), and then 5.7 g of the light-yellow crystalline objective compound (AN-8) was obtained.

The measurement result of the compound by FD-MS showed m/z=520 to $C_{41}H_{28}$=520, therefore the objective compound (AN-8) was confirmed (the yield: 69%).

Example 1

Fabrication of an Organic EL Device

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The cleaned glass substrate having an ITO transparent electrode line was fixed to a substrate holder of a vacuum deposition apparatus, and on the surface, where the ITO transparent electrode line was fixed, of the substrate, a film (hereinafter referred to as TPD232 film) having film thickness of 60 nm of the following N,N'-bis(N,N'-diphenyl-4-aminophenyl)-N,N-diphenyl-4,4'-diamino-1,1'-biphel was formed so as to cover the transparent electrode. The TPD232 film performs as a hole injecting layer. Subsequently, a layer having layer thickness of 20 nm of the following N,N,N',N' tetra(4-biphenyl)-diaminobiphenylene was formed (hereinafter referred to as TBDB layer). The layer performs as a hole transporting layer. Subsequently, a film having a film thickness of 40 nm of the aforementioned compound AN-2 was formed as host material by a vapor deposition. Concurrently, as light emitting material, the following amino compound BD1 containing a styryl group was deposited at the ratio by weight between AN-2 and BD 1 of 40:3 by a vapor deposition. The film performs as a light emitting layer. On the film, a film having a Alq film thickness of 10 nm was formed. The film performs as an electron injecting layer. Further, a film (film thickness: 10 nm) of Alq:Li (the source of lithium: manufactured by SAES GETTERS Company) as an electron injecting layer was formed by binary vapor deposition of Li as a reductive dopant and the following Alq. On the Alq:Li film, Al metal was deposited to form a metal cathode, therefore, an organic EL device was fabricated.

The device was tested by passing electric current, an emission luminance of 615 cd/m² and a current efficiency of 6.5 cd/A was observed at a voltage of 5.76V and a current density of 10 mA/cm². In addition, when the EL device was continuously tested by passing electric current at an initial luminance of 1,000 cd/m², the results of the half-lifetime are shown in Table 1.

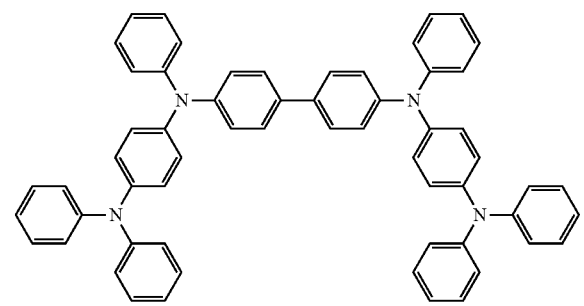

TPD232

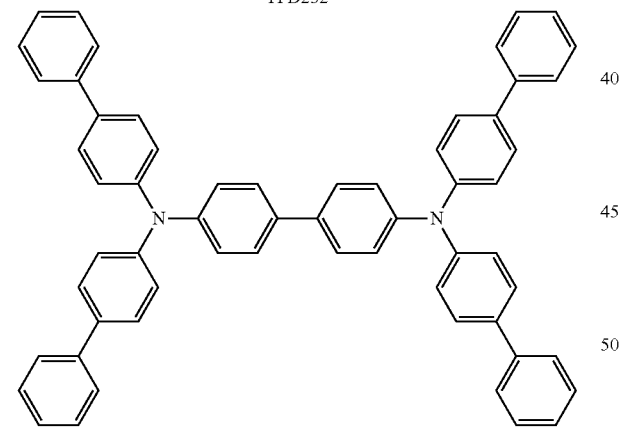

TBDB

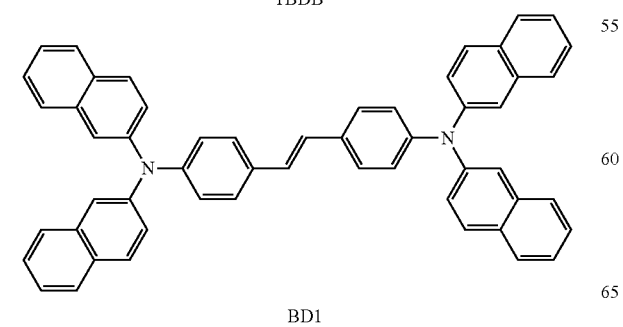

BD1

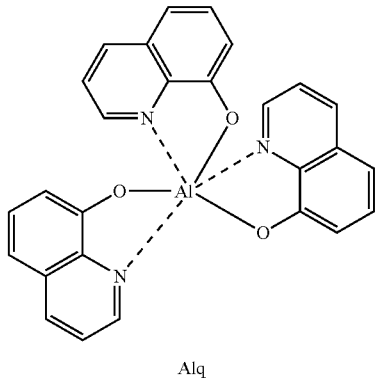

Alq

Examples 2 to 4

Fabrication of Organic EL Devices

Organic EL devices were fabricated similar to Example 1 except that the compounds described in Table 1 were used in place of the compound (AN-2).

The devices obtained were tested by passing electric current similar to the example 1, the results of the half-lifetime measured at an initial luminance of 1,000 cd/m², are shown in Table 1.

Comparative Example 1 to 3

Organic EL devices were fabricated similar to the example 1 except that the following compounds an-1 (Comparative Example 1), an-2 (Comparative Example 2) and an-3 (Comparative Example 3) were used in place of the compound (AN-2).

The devices obtained were tested by passing electric current similar to the example 1, the results of the half-lifetime measured at an initial luminance of 1,000 cd/m², were described in Table 1.

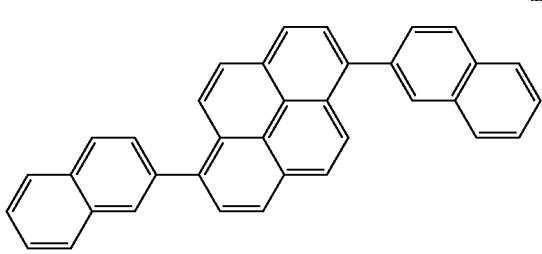

an-1

-continued

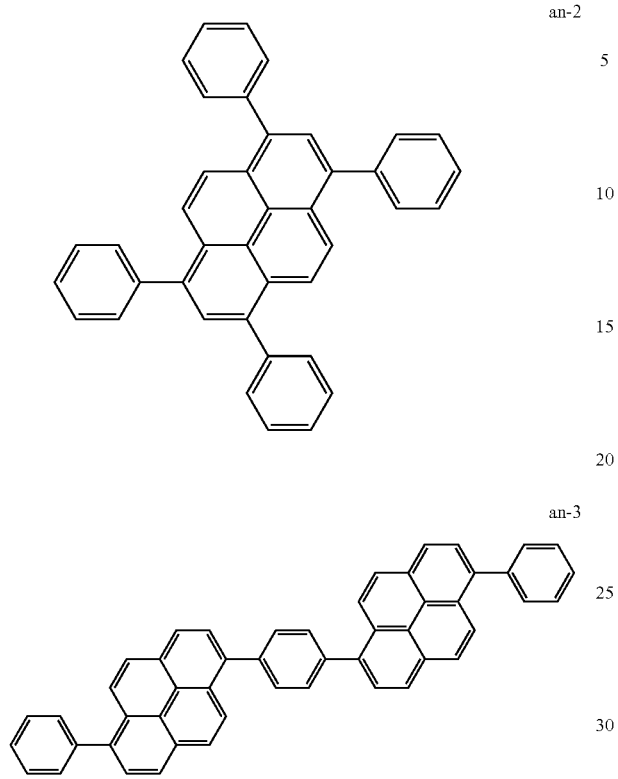

an-2 an-3

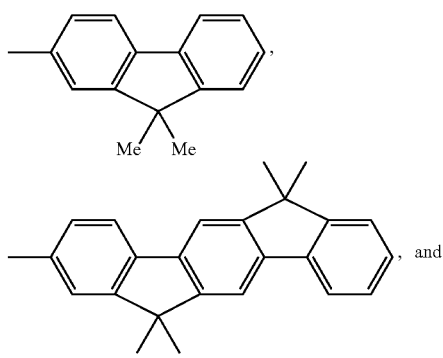

wherein, Ar and Ar' each represents a substituted or unsubstituted aromatic group exclusive of a pyrenyl group, and each of Ar and Ar' is an aromatic group selected from the group consisting of phenyl group, 1-naphthyl group, 2-naphthyl group, 1-anthryl group, 2-anthryl group, 9-anthryl group, 9-(10-phenyl)anthryl group, 9-(10-naphthyl-1-yl)anthryl group, 9-(10-naphthyl-2-yl)anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, 3-methyl-2-naphthyl group, 4-methyl-1-naphthyl group, 4-methyl-1-anthryl group,

TABLE 1

|  | Material Forming a Light Emitting Layer | Driving Voltage (V) | Luminance (cd/m$^2$) | Current Efficiency (cd/A) | Chromaticity Coordinate (x, y) | Half-Lifetime (hours) |
|---|---|---|---|---|---|---|
| Example 1 | AN-2/BD1 | 5.76 | 615 | 6.15 | (0.151, 0.174) | 2800 |
| Example 2 | AN-3/BD1 | 5.79 | 611 | 6.11 | (0.151, 0.177) | 2000 |
| Example 3 | AN-9/BD1 | 5.64 | 645 | 6.45 | (0.148, 0.198) | 1700 |
| Example 4 | AN-8/BD1 | 5.86 | 616 | 6.16 | (0.147, 0.183) | 1500 |
| Comparative Example 1 | an-1/BD1 | 6.85 | 531 | 5.31 | (0.170, 0236) | 490 |
| Comparative Example 2 | an-2/BD1 | 6.89 | 550 | 5.50 | (0.199, 0.230) | 800 |
| Comparative Example 3 | an-3/BD1 | 6.89 | 558 | 5.58 | (0.159, 0229) | 700 |

Industrial Applicability

As aforementioned in detail, an organic EL device employing a compound having an asymmetric pyrene derivative of the present invention exhibits a great efficiency of light emission and has a long lifetime.

Therefore, they are highly applicable as the organic EL devices supposed to be used continuously for long years.

What is claimed is:

1. An asymmetric pyrene derivative represented by formula (2):

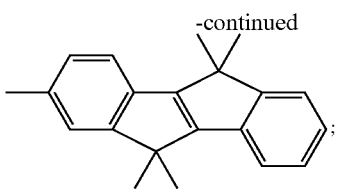

L and L' each represents a substituted or unsubstituted phenylene group, a substituted or unsubstituted naphthalenylene group, a substituted or unsubstituted fluorenylene group, or a substituted or unsubstituted dibenzosilolylene group;

m represents an integer of 0 to 2;

s represents an integer of 0 to 2; and

L' or Ar' bonds to any one of 2 to 10 positions of pyrene;

(3') Ar=Ar', L=L', m=s, t=1, and both L and L' or pyrene each bonds respectively to different positions of Ar and Ar', or (4') Ar=Ar', L=L', m=s, t=1, and both L and L' or pyrene each bonds to the same positions of Ar and Ar', excluding a case where L' or Ar' bonds to 6 position of pyrene, provided that symmetric pyrene derivatives are excluded.

2. The asymmetric pyrene derivative according to claim 1, which is a light emitting material suitable for an organic electroluminescence device.

3. The asymmetric pyrene derivative according to claim 1, which is a host material suitable for an organic electroluminescence device.

4. An organic electroluminescence device which comprises at least one organic thin film layer including a light emitting layer sandwiched between a pair of electrodes consisting of an anode and a cathode, wherein the organic thin film layer comprises the asymmetric pyrene derivative according to claim 1.

5. The organic electroluminescence device according to claim 4, wherein the light emitting layer comprises the asymmetric pyrene derivative as a host material.

6. The organic electroluminescence device according to claim 4, wherein the light emitting layer further comprises an arylamine compound.

7. The organic electroluminescence device according to claim 4, wherein the light emitting layer further comprises a styrylamine compound.

8. An asymmetric pyrene derivative represented by formula (2):

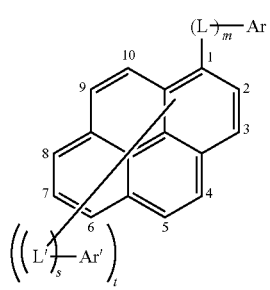

(2)

wherein, Ar and Ar' each represents a substituted or unsubstituted aromatic group exclusive of a pyrenyl group, and each of Ar and Ar' is an aromatic group selected from the group consisting of phenyl group, 1-naphthyl group, 2-naphthyl group, 1-anthryl group, 2-anthryl group, 9-anthryl group, 9-(10-phenyl)anthryl group, 9-(10-naphthyl-1-yl)anthryl group, 9-(10-naphthyl-2-yl)anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, 3-methyl-2-naphthyl group, 4-methyl-1-naphthyl group, 4-methyl-1-anthryl group,

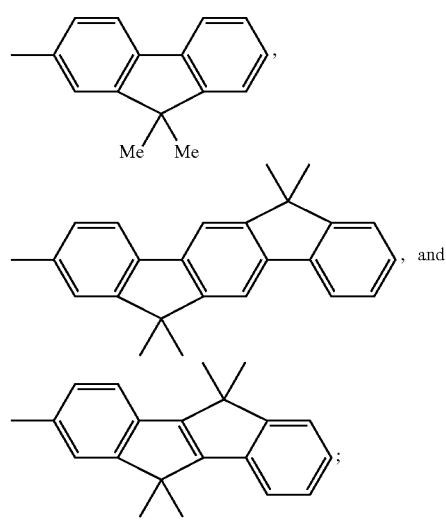

L and L' each represents a substituted or unsubstituted naphthalenylene group, a substituted or unsubstituted fluorenylene group, or a substituted or unsubstituted dibenzosilolylene group;

m represents an integer of 0 to 2;

s represents an integer of 0 to 2;

t represents an integer of 0 to 4; and

L' or Ar' bonds to any one of 2 to 10 positions of pyrene;

provided that when t is an odd number, Ar, Ar', L, and L' satisfy the following requirement (1'), (2'), (3') or (4'):

(1') Ar≠Ar' and/or L≠L' (wherein ≠ means that each group has a different structure), (2') Ar=Ar', L=L', and m≠s and/or t≠1, (3') Ar=Ar', L=L', m=s, t=1, and both L and L' or pyrene each bonds respectively to different positions of Ar and Ar', or (4') Ar=Ar', L=L', m=s, t=1, and both L and L' or pyrene each bonds to the same positions of Ar and Ar', excluding a case where L' or Ar' bonds to 6 position of pyrene, and provided that when t=0, then m=0 and Ar is 9-(10-naphthyl-2-yl)anthryl group, or m is 1 or 2, L is:

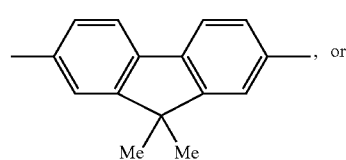

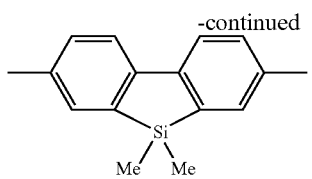

and Ar is the aromatic group selected from the groups defined above; provided that symmetric pyrene derivatives are excluded.

9. The asymmetric pyrene derivative according to claim 8, which is a light emitting material suitable for an organic electroluminescence device.

10. The asymmetric pyrene derivative according to claim 8, which is a host material suitable for an organic electroluminescence device.

11. An organic electroluminescence device which comprises at least one organic thin film layer including a light emitting layer sandwiched between a pair of electrodes consisting of an anode and a cathode, wherein the organic thin film layer comprises the asymmetric pyrene derivative according to claim 8.

12. The organic electroluminescence device according to claim 11, wherein the light emitting layer comprises the asymmetric pyrene derivative as a host material.

13. The organic electroluminescence device according to claim 11, wherein the light emitting layer further comprises an arylamine compound.

14. The organic electroluminescence device according to claim 11, wherein the light emitting layer further comprises a styrylamine compound.

15. An asymmetric pyrene derivative represented by formula (2):

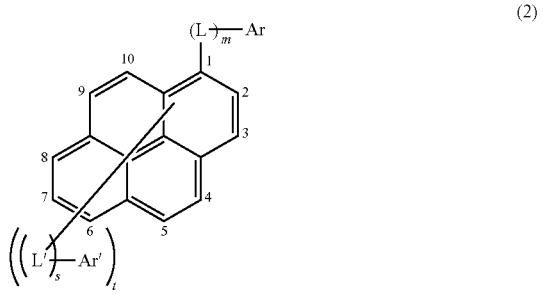

(2)

wherein, Ar and Ar' each represents a substituted or unsubstituted aromatic group exclusive of a pyrenyl group, and each of Ar and Ar' is an aromatic group selected from the group consisting of phenyl group, 1-naphthyl group, 2-naphthyl group, 1-anthryl group, 2-anthryl group, 9-anthryl group, 9-(10-phenyl)anthryl group, 9-(10-naphthyl-1-yl)anthryl group, 9-(10-naphthyl-2-yl)anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, 3-methyl-2-naphthyl group, 4-methyl-1-naphthyl group, 4-methyl-1-anthryl group,

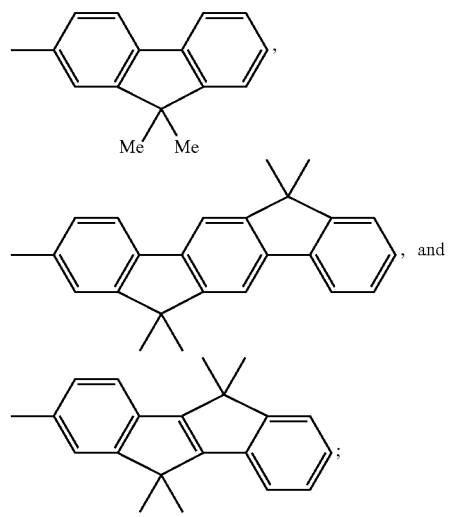

L and L' each represents a substituted or unsubstituted phenylene group, a substituted or unsubstituted naphthalenylene group, a substituted or unsubstituted fluorenylene group, or a substituted or unsubstituted dibenzosilolylene group;

m represents an integer of 0 to 2;

s represents an integer of 0 to 2;

t represents 1, 2, 3, or 4; and

L' or Ar' bonds to any one of 2 to 10 positions of pyrene;

provided that when t is an odd number, Ar, Ar', L and L' satisfy the following requirement (1'), (2'), (3') or (4'):

(1') Ar≠Ar' and/or L≠L' (wherein ≠ means that each group has a different structure), (2') Ar=Ar', L=L', and m≠s and/or t≠1, (3') Ar=Ar', L=L', m=s, t=1, and both L and L' or pyrene each bonds respectively to different positions of Ar and Ar', or (4') Ar=Ar', L=L', m=s, t=1, and both L and L' or pyrene each bonds to the same positions of Ar and Ar', excluding a case where L' or Ar' bonds to 6 position of pyrene; and provided that symmetric pyrene derivatives are excluded.

16. The asymmetric pyrene derivative according to claim 15, which is a light emitting material suitable for an organic electroluminescence device.

17. The asymmetric pyrene derivative according to claim 15, which is a host material suitable for an organic electroluminescence device.

18. An organic electroluminescence device which comprises at least one organic thin film layer including a light emitting layer sandwiched between a pair of electrodes consisting of an anode and a cathode, wherein the organic thin film layer comprises the asymmetric pyrene derivative according to claim 15.

19. The organic electroluminescence device according to claim 18, wherein the light emitting layer comprises the asymmetric pyrene derivative as a host material.

20. The organic electroluminescence device according to claim 18, wherein the light emitting layer further comprises an arylamine compound.

21. The organic electroluminescence device according to claim 18, wherein the light emitting layer further comprises a styrylamine compound.

* * * * *